United States Patent [19]
Odawara

[11] Patent Number: 5,989,819
[45] Date of Patent: Nov. 23, 1999

[54] METHOD FOR QUANTITATIVELY DETERMINING AN ANTIBODY HAVING THE ABILITY TO INHIBIT THE ACTIVITY OF A REVERSE TRANSCRIPTASE

[75] Inventor: Fumitomo Odawara, Mishima, Japan

[73] Assignee: Asahi Kasei Kogyo Kabushiki Kaisha, Osaka, Japan

[21] Appl. No.: 08/952,282

[22] PCT Filed: May 24, 1996

[86] PCT No.: PCT/JP96/01407

§ 371 Date: Nov. 18, 1997

§ 102(e) Date: Nov. 18, 1997

[87] PCT Pub. No.: WO96/37781

PCT Pub. Date: Nov. 28, 1996

[51] Int. Cl.$^6$ ............................... C12Q 1/68; C12Q 1/70
[52] U.S. Cl. ...................................... 435/6; 435/5
[58] Field of Search ............................................ 435/5, 6

[56] References Cited

U.S. PATENT DOCUMENTS 4,942,122  7/1990  Imagawa et al. ........................... 435/5

FOREIGN PATENT DOCUMENTS

| 0 392 459 | 10/1990 | European Pat. Off. . |
| 0 480 408 | 4/1992 | European Pat. Off. . |
| 4-148698 | 5/1992 | Japan . |

OTHER PUBLICATIONS

T. Otake et al., "HIV isolation and clinical markers on the seropositive subjects", pp. 1287–1294, The Journal of the Japanese Association for Infectious Diseases, vol. 64, No. 10, 1990.

D.A. Paul et al., "Correlation of serum HIV antigen and antibody with clinical status in HIV–infected patients", pp. 357–363, Journal of Medical Virology, vol. 22, 1987.

K. Sano et al., "Antibody that inhibits human immunodeficiency virus reverse transcriptase and association with inability to isolate virus", pp. 2415–2417, Journal of Clinical Microbiology, vol. 25, No. 12, Dec. 1987.

L.A. Kohlstaedt et al., "Crystal structure at 3.5 A resolution of HIV–1 reverse transcriptase complexed with an inhibitor", pp. 1783–1790, Science, vol. 256, Jun. 26, 1992.

A.L. Devico et al., "Mechanism of enzyme inhibition mediated by anti–reverse transcriptase antibodies from HIV type 1–infected individuals", pp. 953–960, AIDS Research and Human Retroviruses, vol. 10, No. 8, 1994.

T. Nakano et al., "An improved non–radioisotopic reverse transcriptase assay and its evaluation", pp. 923–931, The Journal of the Japanese Association for Infectious Diseases, vol. 68, No. 7, 1994.

Urabe et al., *J. Clin. Microbiol.* 32(8):1870–1875, Aug. 1994.

Sano et al., *Int. Conf. AIDS (Japan)*, Aug. 7–12, 1994, p. 111, Abstract No. PA0323.

*Primary Examiner*—Robert D. Budens
*Attorney, Agent, or Firm*—Young & Thompson

[57] ABSTRACT

Disclosed is a method for quantitatively determining an antibody, contained in a biological sample, having the ability to inhibit the activity of a reverse transcriptase derived from an HIV, comprising: reacting a hybridization product, immobilized on a solid phase, of a primer consisting essentially of oligodeoxythymine nucleotide and an RNA template consisting essentially of adenine ribopolynucleotide with a reverse transcriptase derived from HIV, to thereby bind the reverse transcriptase to the hybridization product; conducting a synthesis of a DNA complementary to the RNA template from a deoxymononucleotide triphosphate in the presence of the reverse transcriptase activity-inhibiting antibody; and measuring the amount of the synthesized DNA and quantitatively determining the above-mentioned antibody, based on the measured amount of the synthesized DNA. The method of the present invention can be performed with ease and with high reproducibility in classifying and quantitatively determining the antibodies against the epitopes of a viral reverse transcriptase. By the method of the present invention, not only the virus having mutated during a latent period thereof, and the properties which the virulis exhibits as a result of the mutation, but also a virus having acquired drug resistance as a result of the administration of the drugs to the host, can be studied by quantitatively determining the antibodies. Further, it has also become possible to accurately and promptly determine the changes in the infected host, such as the change in the ability to produce antibodies, which occur in accordance with the progression of illness.

12 Claims, No Drawings

METHOD FOR QUANTITATIVELY DETERMINING AN ANTIBODY HAVING THE ABILITY TO INHIBIT THE ACTIVITY OF A REVERSE TRANSCRIPTASE

This application is a national stage application of international application Ser. No. PCT/JP96/01407, filed May 24, 1996.

BACKGROUND OF THE INVENTION

1. Field of the Invention

The present invention relates to a method for quantitatively determining an antibody, contained in a biological sample, having the ability to inhibit the activity of a reverse transcriptase derived from a human immunodeficiency virus (HIV). More particularly, the present invention is concerned with a method for quantitatively determining an antibody, contained in a biological sample, having the ability to inhibit the activity of a reverse transcriptase derived from an HIV, which comprises the steps of: reacting a hybridization product (immobilized on a solid phase) of a primer consisting essentially of oligodeoxythymine nucleotide and an RNA template consisting essentially of adenine ribopolynucleotide with a reverse transcriptase derived from HIV in an aqueous reaction system, to bind the reverse transcriptase to the hybridization product, thereby obtaining a hybridization product-bound reverse transcriptase; conducting a synthesis of a complementary deoxyribonucleic acid to the RNA template from a deoxymononucleotide triphosphate added to the aqueous reaction system under the action of the hybridization product-bound reverse transcriptase in the presence of the antibody having the ability to inhibit the activity of the reverse transcriptase; and measuring the amount of the synthesized complementary deoxyribonucleic acid and quantitatively determining the antibody having the ability to inhibit the activity of the reverse transcriptase, based on the measured amount of the synthesized complementary deoxyribonucleic acid. More particularly, according to the present invention, there is provided a method for quantitatively determining an antibody, contained in a biological sample, having the ability to inhibit the activity of a reverse transcriptase derived from an HIV, in the above-mentioned steps, wherein the reverse transcriptase is reacted with the antibody present in the aqueous reaction system, and wherein the reaction of the reverse transcriptase with the antibody is conducted after the binding of the reverse transcriptase to the hybridization product and before the addition of the deoxymononucleotide triphosphate; or before the binding of the reverse transcriptase to the hybridization product and before the addition of the deoxymononucleotide triphosphate; or after the binding of the reverse transcriptase to the hybridization product and simultaneously with the addition of the deoxymononucleotide triphosphate and antibody.

Conventionally, it has been difficult to classify the antibodies against the viral antigens into groups according to the types of the epitopes which the antibodies recognize, and quantitatively determine each of the groups of antibodies. However, the present invention provides an easy and highly reproducible method for classifying and quantitatively determining the antibodies against the epitopes of a viral reverse transcriptase. Using the method of the present invention, not only the virus which has mutated during a latent period thereof, and the properties which the virus exhibits as a result of the mutation, but also a virus which has acquired drug resistance as a result of the administration of the drugs to the host, can be studied by quantitatively determining the antibodies. Further, by the method of the present invention, it has also become possible to accurately and promptly determine the changes in the infected host, such as the change in the ability to produce antibodies, which occur in accordance with the progression of illness. In addition, the above-mentioned method is advantageous in that the biological samples used are easily available, and that cumbersome procedures, such as culturing of the virus, are not required. Therefore, the method of the present invention is effective for the diagnosis and the like of HIV which necessarily include testings for an extremely large number of test items. Further, the method of the present invention can be advantageously used for the study of HIV infection because an antibody is more stable than a viral antigen and a high biosafety can be achieved by the treatment of the biological samples with a surfactant.

2. Prior Art

With respect to patients infected with human immunodeficiency virus (HIV), an infallible therapeutic method has not yet been developed. The latent period of HIV is said to be from 5 to 10 years after the infection with HIV, and the process toward the onset of the disease after the infection has not yet been elucidated. A method for predicting the time of the onset of AIDS has not yet been developed and, thus, in most cases, the diagnosis of the HIV infection is simply to determine whether a person is infected with HIV or not.

Conventionally, for determining the HIV infection, there was generally used a method of detecting an antigen or an antibody present in the body fluid, such as serum, plasma, saliva and urine of the patient infected with HIV.

The method of detecting an antigen comprises, for example, immobilizing an antibody against HIV envelope protein on a solid phase carrier, such as a polystyrene ball, and adding serum as a biological sample to the carrier to bind the HIV protein present in the serum to the antibody to thereby obtain an antibody-HIV protein complex. Then, the obtained antibody-HIV protein complex was reacted with an enzyme-labeled antibody which recognizes a different site of the HIV protein, to thereby obtain an antibody-HIV protein-antibody-enzyme complex. The activity of the enzyme ultimately present on the solid phase carrier is measured to thereby confirm the presence of the HIV in the serum of the patient. The diagnostic test kit for HIV infection which uses the principle of the above-mentioned method is commercially available (HIV antibody EIA Abbott, manufactured and sold by Abbott diagnostics, U.S.A.) and is applied in the medical practice.

The above-mentioned method of detecting an antigen based on the enzyme immunoassay, however, is disadvantageous in that the viral antigen can be detected only during the acute infection period immediately after the infection with HIV or when the patient is suffering from viremia as a result of the onset of AIDS. Therefore, the detection of an antigen during the latent period of the virus is almost impossible and, the use of this principle as a marker for determining the condition of the HIV-infected patient or for determining the properties of the virus is only possible during the above-mentioned specific periods in which the detection of the virus is possible.

There are other methods for detecting a viral antigen during the latent period of the virus. In one of these methods, peripheral lymphocytes are isolated from a patient whose infection with HIV is suspected, and the lymphocytes are infected to uninfected Molt-4 cells, followed by subculturing of the cells. During the culturing of the cells, the above-mentioned enzyme immunoassay or the measurement of the reverse transcriptase activity was periodically performed with respect to the supernatant of the cell culture, to thereby determine the presence of the virus (see The Journal of the Japanese Association for Infectious Diseases, vol. 64, No. 10, 1287–1294, 1990, Japan). However, this method is disadvantageous not only in that the intended virus is not always found in the peripheral lymphocytes isolated from the patient, but also in that the properties of each of the isolated viruses must be individually examined in order to obtain a marker for the onset of the disease. Further, it takes approximately two weeks until the results of the assay are obtained. Also, this method is disadvantageous in that a greatly laborious procedure for subculturing the cells and large expense for repeating the assay throughout the latent period of the virus, that is said to be as long as 5 to 10 years, are required. Therefore, the above-mentioned method is not generally in practice for the diagnosis of the HIV infection where the treatment of numerous biological samples are required.

On the other hand, there can also be mentioned a method of detecting an antibody against HIV in the serum of the patient as an alternative to a method of detecting an antigen. In practice, a method of detecting an antibody by enzyme immunoassay has been employed, and a test kit for determination of an antibody is commercially available (Du Pont HIV ELISA, manufactured and sold by Du Pont, U.S.A.). In a specific example of a method of determining an antibody, diluted serum of a patient as a biological sample is added to a 96-well microtiter plate on which an HIV antigen is immobilized, and the microtiter plate is incubated at room temperature for 2 hours, followed by washing of the microtiter plate to remove the unreacted samples. Then, an enzyme-labeled anti-human antibody is added to the microtiter plate and incubated at room temperature for 1 hour, followed by washing of the microtiter plate to remove the unreacted antibody. An enzyme substrate is added to the microtiter plate for conducting a reaction at 37° C. for 30 minutes to develop a color which is measured in terms of absorbance by means of a plate reader or the like, and the antibody is detected from the absorbance value. An antibody produced during the latent period of the HIV infection can be detected by this method, and thus, it is used in practice for screening the patients infected with HIV.

There is a report on the tendency that the quantity of an antibody against p24 antigen (which is a core protein of HIV) decreases as the condition of a patient changes from Asymptotic Carrier (AC) to AIDS-related Complex (ARC) and then to the onset of AIDS (see Paul, D. A. et al, J. Med. Viol., 22: 357–363, 1987). Therefore, the quantitative determination of the antibody can be used not only for screening the infected patients, but also as a marker for determining the condition of the patient. However, in the above-mentioned method, the antibodies against the viral proteins, such as gp120, gp41, p24, p15 and the like, are all detected at once and, therefore, the measurement is not made with respect to an antibody against a particular epitope. This method is disadvantageous in that it is impossible to determine a true change in the amount of an antibody occurring in accordance with the viral mutation after the infection and, thus, the antibody detected by this method has not been used as an index of the condition of the infected person during the latent period of the virus, or as an index of the properties of the virus at a certain point in time.

Several methods have been developed for classifying the antibodies according to the epitopes which the antibodies recognize, and quantitatively determining their amount in order to study the relationship between the amount of the antibodies and the condition of a patient. For example, in one of the methods, several peptides corresponding to the HIV antigen proteins are synthesized, and the reactivity of the antibodies contained in a biological sample obtained from a patient with the synthesized peptides has been studied. Since an antibody recognizes a three dimensional structure of an antigen, the synthesized peptide as an antigenic determinant cannot always be used for the determination of an antibody against an antigen derived from the virus.

As an alternative method for determining an antibody against an antigen at a specific epitope thereof, a method for quantitatively determining an antibody capable of inhibiting a reverse transcriptase activity has been proposed. For example, an antibody capable of inhibiting the reverse transcriptase activity which is found in the serum of an HIV-infected person, is added to the reaction mixture for measuring the reverse transcriptase activity, and the amount of the antibody is determined from the degree of inhibition of the enzyme activity which is measured with respect to a specific amount of the enzyme (see Sano, K., et al, J. Clin. Microbiol. Vol.25, NO. 12, 2415–2417, 1987; and Unexamined Japanese Patent Application No. 3-47098). This method is different from the above-mentioned methods in that, by detecting only an antibody inhibiting the activity of the reverse transcriptase as an antigen, the antibody against a particular group of epitopes is determined.

However, in general, this method is practiced in substantially the same manner as in the methods for determining the enzyme activities using the radioisotopes. Therefore, special facilities are required and moreover, the measuring procedure is complicated, so it is not suitable for diagnosis of HIV infection where a number of samples must be treated. In addition, this method simply limits the target of detection to a specific group of antibodies which suppresses the reverse transcriptase activity, but is not a method in which antibodies recognizing the active center of the reverse transcriptase as an antigen which active center is less likely to mutate, are individually specified and determined in accordance with the respective epitopes of the antigen. Therefore, it is difficult to trace the mutated virus or the amount of an antibody produced during the latent period of the virus by determining the antibody.

There has also been provided a method for determining, on a solid phase, an antibody having the ability to inhibit the activity of a reverse transcriptase. For example, a hybridization product of poly A and oligo dT is immobilized on a well of a microtiter plate for enzyme immunoassay (hereinafter, frequently referred to simply as "EIA") having 96 wells, and, subsequently, a reverse transcriptase, deoxythyminemononucleotide, biotinylated deoxyuridinemononucleotide, and a biological sample containing an antibody are charged to the well to thereby perform a reaction. All reactants remaining unreacted are removed by washing and then, the elongated chains comprising biotinylated nucleic acids are reacted with streptoabidine-alkaline phosphatase. After removing the reactants remaining unreacted by washing, the alkaline phosphatase activity present on the solid phase was determined, thereby determining the antibodies capable of inhibiting the activity of the reverse transcriptase (see European Patent Application No. 0 480 408A1).

However, it is to be noted that a conventional reverse transcriptase derived from HIV has ribonuclease H (RNase H) activity which is the ability to decompose only RNA of the hybridization product of DNA and RNA (see L. A. Kohlstaedt, et al., Science, Vol. 256, 1783–1790, 1992). Therefore, when a reverse transcriptase is reacted by simply bringing the reverse transcriptase into contact with the hybridization product of DNA and RNA immobilized on a solid phase in order to produce a complex of the reverse transcriptase and the hybridization product, the digestion of the hybridization product with the RNase H activity is likely to occur, leading to a difficulty in the detection of the antibody.

With respect to the determination of an antibody capable of inhibiting the reverse transcriptase activity, a method has recently been developed in which a particular group of antibodies is quantitatively determined by means of epitopes which the antibodies recognize, wherein a group of antibodies which competes with a template-primer complex relative to the reverse transcriptase or a group of antibodies which inhibits the binding of the reverse transcriptase to a template-primer complex are specified and determined (see Anthony, L. D. et al, AIDS Research and Human Retroviruses, Vol. 10, Number 8, 953–960, 1994). Specifically, the reverse transcriptase activity is measured using a substrate labeled with a radioisotope in the presence of diluted serum containing an antibody capable of inhibiting the enzyme activity. More particularly, the amount of the template-primer complex used in the reaction system is varied and the respective enzyme activities obtained by the variance of the amount of the template-primer complex is measured, so that the individual amount of the inhibited enzyme activity with respect to each amount of the template-primer is determined. Either the competitive reaction with the recognition site of the reverse transcriptase between the template-primer complex and the antibody, or the inhibition of the binding of the reverse transcriptase to the template-primer complex by the antibody can be determined. However, the reverse transcriptase used in this method is an enzyme prepared from HIV particles and, therefore, the enzyme reaction is measured in a reaction system contaminated by the template-primer complex derived from the virus. Therefore, there is a problem in that an accurate and reproducible measurement of the inhibitory action of an antibody cannot be determined. Also this method has a problem of biohazards.

Recently, a further method has been developed in which a reverse transcriptase activity is measured using a template-primer complex immobilized on a solid phase (see Nakano et al., The Journal of the Japanese Association for Infectious Diseases, vol. 68, No. 7, 923–931, 1994, Japan). In this method, a template-primer complex is immobilized on a well of a microtiter plate having 96 wells, and a reverse transcriptase and biotinylated deoxyuridine triphosphate (biotinylated dUTP) as a substrate for DNA synthesis are charged into the wells and a reverse transcriptase reaction is conducted. The biotinylated DNA finally formed on the solid phase is determined by a non-radioisotopic method.

As mentioned above, it is difficult to study the mutation of the virus, based on an antibody produced in a body of an infected person, because the antibody is polyclonal. Further, a possible method for solving this problem, that is, a method for classifying anti-bodies against the viral antigen into groups according to the types of epitopes which the antibodies recognize is also difficult to perform. Therefore, with respect to HIV infection, a reliable method of using an anti-body as a diagnostic marker, in which the existence of the mutated virus or the condition of the infected person is fully reflected, has not yet been developed. Accordingly, the diagnosis using an antibody has not been put into practical use, but instead has been conducted only on the laboratory level. Further, these methods are complicated and have been adversely affecting the researches in this field in regard to cost and labor.

With respect to the above-mentioned groups of antibodies which recognize the proteins of the viral antigen, if an easy and reproducible method for classifying the antibodies according to the epitopes which the antibodies recognize and for quantitatively determining the antibodies is developed, it will become possible to efficiently study the correlation between the viral properties and the condition of the patient, on the basis of the antibodies, instead of viruses which are difficult to detect during their latent period, such as the viruses in the patients having AC symptoms. Further, the studies on viruses having undergone continuous mutation for a period of time as long as 5 to 10 years and viruses having acquired drug resistance as a result of the administration of the drugs to the host will be possible through quantitative determination of the antibodies.

Further, an accurate and prompt determination of the changes in the infected host, such as the change in the ability to produce an antibody, which occur in accordance with the progression of the illness will be possible. In addition, due to the use of the antibody, not only can a high availability of the biological samples be achieved, but also there is no need for cumbersome procedures, such as culturing of the virus, so that for the diagnosis of HIV and the like which need testing for a large number of test items, such a method will be able to be advantageously used. Further, in view of the fact that the stability of an antibody is higher than that of a viral antigen, a high biosafety will be able to be achieved by a possible treatment of the biological samples with a surfactant.

Therefore, it has been strongly desired to develop an easy and highly reproducible measuring system in which the antibodies against the proteins of the viral antigens can be classified into groups of antibodies according to the types of epitopes which the antibodies recognize and the quantitative determination of the antibodies can be conducted.

SUMMARY OF THE INVENTION

The present inventor has made extensive and intensive studies with a view toward solving the above-mentioned problems in the art. As a result, it has unexpectedly been found that a measurement of a reverse transcriptase activity can be achieved by a system where the enzyme reaction is divided into two stages, that is, a first stage: binding of a hybridization product of an RNA template and a primer (hereinafter, frequently referred to simply as "template-primer") to a reverse transcriptase; and a second stage: synthesis of a DNA complementary to the RNA template. Especially, it has been found that in the first stage of the reverse transcriptase reaction, the binding of the template-primer to the reverse transcriptase can be stably conducted with high reproducibility, preferably in the presence of a water-soluble metal salt capable of producing bivalent metal ions. Further, it has also unexpectedly been found that, utilizing the modes of the inhibition expressed by the antibodies having the ability to inhibit the reverse transcriptase activity, the reverse transcriptase inhibiting antibodies can be classified into three groups, i.e., a first group of antibodies, a second group of antibodies and a third group of antibodies, in accordance with the epitopes which are respectively recognized by the antigens. The present invention has been completed, based on the above novel findings. The above-mentioned first group, second group and third group of antibodies are, respectively, identified as follows:

Group 1: a group of antibodies having the ability to inhibit a chain elongation of a complementary DNA to an RNA template by an irreversible binding of an antibody (contained in a biological sample) to a reverse transcriptase;

Group 2: a group of antibodies having the ability to inhibit the binding of a reverse transcriptase to a template-primer; and Group 3: a group of antibodies having the ability to inhibit a DNA-chain elongation by the reaction of an antibody (contained in a biological sample) to a reverse transcriptase which is synthesizing a DNA.

Accordingly, it is an object of the present invention to provide a method for quantitatively determining an antibody having the ability to inhibit the activity of a reverse transcriptase derived from a virus, wherein the antibodies are classified with ease and with high reproducibility in accordance with the type of epitope of the reverse transcriptase derived from the virus, and quantitatively determining the classified antibodies.

The foregoing and other objects, features and advantages of the present invention will be apparent from the following detailed description and appended claims.

DETAILED DESCRIPTION OF THE INVENTION

In one aspect (hereinafter, frequently referred to as "first embodiment") of the present invention, there is provided a method for quantitatively determining an antibody, contained in a biological sample, having the ability to inhibit the activity of a reverse transcriptase derived from a human immunodeficiency virus (HIV), which comprises the steps of:

(A) reacting a hybridization product of a primer consisting essentially of oligodeoxythymine nucleotide immobilized on a solid phase and an RNA template consisting essentially of adenine ribopolynucleotide with a reverse transcriptase derived from HIV in an aqueous reaction system, to bind the reverse transcriptase to the hybridization product, thereby obtaining a first reaction mixture containing a hybridization product-bound reverse transcriptase, (B) removing the reverse transcriptase remaining unreacted from the first reaction mixture by washing, and reacting a biological sample containing an antibody having the ability to inhibit the activity of a reverse transcriptase derived from HIV with the hybridization product-bound reverse transcriptase, to bind the antibody to the hybridization product-bound reverse transcriptase, thereby obtaining a second reaction mixture containing the antibody which is bound to the hybridization product-bound reverse transcriptase, (C) removing the antibody remaining unreacted from the second reaction mixture by washing, and adding a deoxymononucleotide triphosphate to the remainder of the second reaction mixture to thereby synthesize a deoxyribonucleic acid complementary to the RNA template, and (D) measuring the amount of the synthesized complementary deoxyribonucleic acid and quantitatively determining the antibody having the ability to inhibit the activity of the reverse transcriptase, based on the measured amount of the synthesized complementary deoxyribonucleic acid.

By the above-mentioned method, a group of antibodies having the ability to inhibit a DNA-chain elongation by the irreversible binding of an antibody (contained in a biological sample) to a reverse transcriptase can be identified.

In another aspect (hereinafter, frequently referred to as "second embodiment") of the present invention, there is provided a method for quantitatively determining an antibody, contained in a biological sample, having the ability to inhibit the activity of a reverse transcriptase derived from a human immunodeficiency virus (HIV), which comprises the steps of:

(E) reacting a biological sample containing an antibody having the ability to inhibit the activity of a reverse transcriptase derived from HIV with a reverse transcriptase derived from HIV in an aqueous reaction system, to bind the reverse transcriptase to the antibody, thereby obtaining a first reaction mixture containing an antibody-bound reverse transcriptase, (F) reacting a hybridization product of a primer consisting essentially of oligodeoxythymine nucleotide immobilized on a solid phase and an RNA template consisting essentially of adenine ribopolynucleotide with the first reaction mixture, to bind the reverse transcriptase to the hybridization product, thereby obtaining a second reaction mixture containing a hybridization product-bound reverse transcriptase, (G) removing all reactants remaining unreacted from the second reaction mixture by washing, and adding a deoxymononucleotide triphosphate to the remainder of the second reaction mixture to thereby synthesize a deoxyribonucleic acid complementary to the RNA template, and (H) measuring the amount of the synthesized complementary deoxyribonucleic acid and quantitatively determining the antibody having the ability to inhibit the activity of the reverse transcriptase, based on the measured amount of the synthesized complementary deoxyribonucleic acid.

By the above-mentioned method, a group of antibodies having the ability to inhibit the binding of a reverse transcriptase to a template-primer can be identified.

In still another aspect (hereinafter, frequently referred to as "third embodiment") of the present invention, there is provided a method for quantitatively determining an antibody, contained in a biological sample, having the ability to inhibit the activity of a reverse transcriptase derived from a human immunodeficiency virus (HIV), which comprises the steps of:

(I) reacting a hybridization product of a primer consisting essentially of oligodeoxythymine nucleotide immobilized on a solid phase and an RNA template consisting essentially of adenine ribopolynucleotide with a reverse transcriptase derived from HIV in an aqueous reaction system, to bind the reverse transcriptase to the hybridization product, thereby obtaining a first reaction mixture containing a hybridization product-bound reverse transcriptase, (J) removing the reverse transcriptase remaining unreacted from the first reaction mixture by washing, and adding to the remainder of the first reaction mixture both a biological sample containing an antibody having the ability to inhibit the activity of a reverse transcriptase derived from HIV and a deoxymononucleotide triphosphate, to thereby cause the antibody to react to the hybridization product-bound reverse transcriptase while synthesizing a deoxyribonucleic acid complementary to the RNA template, and (K) measuring the amount of the synthesized complementary deoxyribonucleic acid and quantitatively determining the antibody having the ability to inhibit the activity of the reverse transcriptase, based on the measured amount of the synthesized complementary deoxyribonucleic acid.

By the above-mentioned method, a group of antibodies having the ability to inhibit a DNA-chain elongation by the reaction of an antibody (contained in a biological sample) to a reverse transcriptase during the DNA-chain elongation can be identified.

In each of the step (A) of the first embodiment, the step (F) of the second embodiment and the step (I) of the third embodiment of the present invention, the reverse transcriptase recognizes the template-primer, and binds to the template-primer. In the method of the present invention, the binding of the reverse transcriptase to the template-primer and the DNA-chain elongation are performed separately. Further, in each of the above-mentioned steps (A), (F) and (I), the binding of the reverse transcriptase to the template-primer can be conducted stably and efficiently in the presence of a water-soluble metal salt capable of producing bivalent metal ions.

With respect to the solid phase carrier used in the present invention, use may be made of a transparent solid phase, a semi-transparent solid phase or an opaque solid phase, and there is no particular limitation as long as a primer consisting essentially of oligo dT can be immobilized on the solid phase carrier. Examples of solid phases used in the present invention include a plate for EIA, magnetic beads, plastic balls for EIA and a tube. Examples of materials for the solid phase carrier used in the present invention include plastics, such as polystyrene, polypropylene, Teflon®, polyethylene, a methylpentene resin (TPX), a fluororesin, an acrylic resin, a polycarbonate, a polyurethane and a polyvinyl chloride resin; metals, such as a stainless steel, aluminum and titanium; a glass; and a rubber.

As examples of methods for immobilizing a nucleic acid on such a solid phase carrier, there can be mentioned a method in which a nucleic acid is adsorbed on a solid phase; a method in which the 5'-terminus of a nucleic acid is chemically bound directly to a solid phase [V. Lund et. al., Nucleic Acids Research, vol. 16, 22, 10861–10880 (1988)]; and a method in which a nucleic acid is modified at the 3'-terminus, 5'-terminus, purine ring or pyrimidine ring thereof with biotin, a hapten, a receptor or the like, and the modified nucleic acid is bound to a ligand, such as avidin and an antibody, which is previously immobilized on a solid phase. By these methods, a nucleic acid can be immobilized on a solid phase carrier with ease.

In the present invention, a primer consisting essentially of oligo dT will be immobilized on a solid phase, and the primer comprises at least three dTs capable of binding to an RNA template consisting essentially of poly A. The primer comprises preferably three or more contiguous dTs, more preferably five or more contiguous dTs, and there is no particular limitation as long as a transcriptional initiation site is substantially recognizable by the reverse transcriptase. It is preferred that the primer consisting essentially of oligo dT contains 3 to 100,000 nucleotides, more preferably from 5 to 100,000 nucleotides. Oligo dT is commercially readily available (from Pharmacia Fine Chemicals AB, Sweden; Sigma Chemical Company, U.S.A.; etc.). In addition, oligo dT can be easily prepared by chemical synthesis, and the preparation of which can be made by requesting a manufacturer (such as TAKARA SHUZO CO., LTD., Japan and NIPPON GENE CO., LTD., Japan) to do so. When oligo dT having a length of 700 or more nucleotides is needed, the oligo dT can be enzymatically prepared on a laboratory scale with ease. For example, oligo dT can be obtained using the above-mentioned commercially available oligo dT as a substrate for an enzyme (T4 RNA ligase; manufactured and sold by TAKARA SHUZO CO., LTD., Japan) which has the activity to bond the phosphate group at the 5'-terminus and the hydroxyl group at the 3'-terminus of a single strand DNA through a phosphodiester bond. Oligo dT can also be obtained by polymerizing deoxythymine nucleotide so as to effect chain extension from the 3'-hydroxyl group of the oligo dT by means of another type of enzyme, such as terminal deoxynucleotidyl transferase (manufactured and sold by TAKARA SHUZO CO., LTD, Japan).

In the present invention, with respect to the RNA template consisting essentially of poly A, there is no particular limitation as long as the sequence of the RNA template is capable of hybridization with a primer immobilized on a solid phase which consists essentially of oligo dT and as long as the reverse transcriptase can recognize the sequence as an RNA template so as to enable a DNA to be synthesized. It is preferred that the template consisting essentially of poly A contains 3 to 100,000 nucleotides, more preferably from 5 to 100,000 nucleotides. Poly A is commercially readily available (for example, from Pharmacia Fine Chemicals AB, Sweden). On the other hand, poly A can be easily prepared by a chemical synthesis and the preparation of which can be made by requesting to a manufacturer (such as TAKARA SHUZO CO., LTD., Japan) to do so. When poly A having a length of 500 or more nucleotides is desired, the poly A can be enzymatically prepared on a laboratory scale with ease. For example, poly A can be obtained using the above-mentioned commercially available poly A as a substrate for an enzyme (T4 RNA ligase; manufactured and sold by TAKARA SHUZO CO., LTD., Japan) which has the activity to bond the phosphate group at the 5'-terminus to the hydroxyl group at the 3'-terminus of a single strand RNA through a phosphodiester bond.

The reverse transcriptase used in the present invention is an enzyme derived from HIV, which has the activity to synthesize from an RNA template a DNA having a nucleotide sequence complementary to the template, and reverse transcriptases derived from HIV Type 1 and HIV Type 2 are known. These reverse transcriptases can be easily obtained by directly separating the enzyme from the HIV virus. For example, a reverse transcriptase can be easily prepared by treating the virus particles of LAV-1 strain, LAV-2 strain, GH-1 strain, GH-2 strain, GH-3 strain, GH-4 strain, GH-5 strain, GH-6 strain, or the like, with a surfactant, such as Triton X-100. If desired, the viral nucleic acids are decomposed and removed by the treatment with a nuclease and the like. In addition, an enzyme obtained by mass expression of a recombinant DNA in *Escherichia coil* is commercially readily available (for example, from SEIKAGAKU KOGYO CO., LTD, Japan). With respect to the reverse transcriptase used in the present invention, it is preferred to use a recombinant reverse transcriptase obtained from *E. coil* which is free from the nucleic acids which function as a template. With respect to the amount of the reverse transcriptase used in the present invention, there is no particular limitation, as long as the residual activity of the reverse transcriptase (%) measured in the presence of a test sample prepared from a biological sample, such as serum, is more than 0%, which is calculated relative to the reverse transcriptase activity (100%) measured without using a test sample. In each of the step (A) of the first embodiment, the step (E) of the second embodiment and the step (I) of the third embodiment, the amount of the reverse transcriptase in the aqueous reaction system is preferably within the range of from 0.1 $\mu$U/ml to 10,000 U/ml, more preferably from 2 $\mu$U/ml to 1,000 U/ml. {In the present invention, the enzyme activity is expressed using a unit "U", wherein 1 U corresponds to the reverse transcriptase activity to incorporate 1 nmol of dTMP in the form of a DNA synthesized by a reverse transcriptase reaction performed using poly(rA)·oligo(dT) as a template-primer, wherein the reaction temperature is 37° C., and the reaction time is 10 minutes (Hout, G. E., 1979, J. Virol. 29, 517).}

In the present invention, examples of reverse transcriptase activity-inhibiting antibodies contained in a biological sample include immumoglobulin A, immumoglobulin G, immumoglobulin M, immumoglobulin D and immumoglobulin E, each having the ability to inhibit the activity of a reverse transcriptase. Examples of biological samples used in the present invention include a living body fluid containing such an antibody, such as serum, plasma, urine, saliva and tears. The biological samples are not particularly limited to these living body fluids. Of these, preferred are serum and plasma.

Each of the above-mentioned biological samples can be used in a dilution ratio in the range of from 1-fold to 1,000,000-fold. It is preferred to use a biological sample in a dilution ratio in the range of from 1-fold to 100,000-fold.

With respect to the deoxymononucleotide triphosphates, examples of non-labeled deoxymononucleotide triphosphates include monodeoxythymidine triphosphate (dTTP); and examples of labeled deoxymononucleotide triphosphates include biotinylated monodeoxyuridine triphosphate (biotinylated dUTP), digoxigenin-labeled monodeoxyuridine triphosphate (digoxigenin-labeled dUTP), tritium-labeled monodeoxythymidine triphosphate ($^3$H-dTTP) and $^{32}$P-labeled monodeoxythymidine triphosphate ($^{32}$P-dTTP). As to how to use these deoxymononucleotide triphosphates, there is no particular limitation, as long as at least one of these deoxymononucleotide triphosphates is used. However, among the above-mentioned deoxymononucleotide triphosphates, it is preferred to use, in combination, a dTTP as a non-labeled deoxymononucleotide triphosphate and a biotinylated dUTP as a labeled deoxymononucleotide triphosphate. With respect to the amount of the non-labeled and/or labeled deoxymononucleotide triphosphate used in the present invention, there is no particular limitation as long as the reverse transcriptase reaction can proceed and the reverse transcriptase activity can be detected from the labeled deoxymononucleotide triphosphate. The detection of a reverse transcriptase activity is possible as long as the amount of the non-labeled deoxymononucleotide triphosphate is within the range of from 0 to 500 molecules, per molecule of the labeled deoxymononucleotide triphosphate.

Hereinbelow, the first embodiment of the present invention will be described in detail.

As mentioned above, in the step (A) of the first embodiment, it is preferred that the binding of the reverse transcriptase to the template-primer is conducted in the presence of a water-soluble metal salt capable of producing bivalent metal ions. As a reaction medium in the reaction system, an aqueous medium is generally used. With respect to the metal salts capable of producing bivalent metal ions in an aqueous medium, examples of metal salts include salts of bivalent metals, such as magnesium (Mg), manganese (Mn), calcium (Ca), zinc (Zn), cadmium (Cd) and copper (Cu). Further, with respect to the water-soluble metal salts capable of producing bivalent metal ions in an aqueous medium, examples of water-soluble metal salts include water-soluble salts, such as a chloride, a fluoride, an iodide, a nitrate, a sulfate and a hydrogencarbonate, of bivalent metals, such as Mg, Mn, Ca, Zn, Cd and Cu. Specific examples of water-soluble metal salts include $MgCl_2$, $MnCl_2$, $CaCl_2$, $ZnCl_2$, $CdCl_2$, $CuCl_2$, $MgSO_4$, $MnSO_4$, $CdSO_4$ and $CuSO_4$. Of these, preferred are $MgCl_2$, $MnCl_2$ and $CaCl_2$. It is preferred that the bivalent metal ions are present in a concentration of from 0.01 mM to 1M, preferably from 0.1 mM to 500 mM, in the aqueous reaction system.

With respect to the pH value of the aqueous reaction system in the step (A) of the first embodiment, there is no particular limitation as long as the pH is adjusted to an optimum pH value for the binding of the reverse transcriptase to the template-primer immobilized on the solid phase. It is preferred that the pH value of the aqueous reaction system is within the range of from 3 to 10, more preferably from 5 to 9. With respect to the buffer for use in the reaction system, there is no particular limitation as long as the buffer is appropriately selected depending on the desired pH value of the reaction system. For example, one or more buffers can be appropriately selected from the group consisting of a Tris buffer, a phosphate buffer, an acetic acid buffer and a Good's buffer. If desired, a salt, such as NaCl and KCl, and an SH group-containing protective reagent, such as dithiothreitol, dithioerythritol and glutathione, may be added to the buffer in the reaction system. Further, depending on the type of the material of a container for accommodating the reaction system therein, a protein (such as albumin and IgG), an amino acid or a polyamino acid (such as lysine and poly-L-lysine) and a surfactant may be added to the reaction system as an adsorption preventive agent for preventing the components of the reaction system from being adsorbed on the inner wall of the container.

With respect to the reaction temperature in the step (A) of the first embodiment, there is no particular limitation as long as the reaction temperature is higher than a temperature at which the solution of the reaction system freezes and at which the reverse transcriptase activity can be measured. However, it is preferred that the reaction temperature is in the range of from 0 to 50° C.

With respect to the reaction time in the step (A) of the first embodiment, there is no particular limitation as long as the binding of a reverse transcriptase to a template-primer is performed to an extent that the bound reverse transcriptase can be detected. However, it is preferred that the reaction time is in the range of from 1 second to 24 hours.

Further, with respect to the reaction conditions for the binding of the reverse transcriptase with the antibody in the step (B) of the first embodiment, there is no particular limitation as long as the reaction conditions are similar to those which are generally employed for an antigen-antibody reaction. For example, with respect to the pH value of the reaction system in the step (B) of the first embodiment, there is no particular limitation as long as the pH is adjusted to an optimum pH value for the antigen-antibody reaction. However, it is preferred that the pH value of the reaction system is in the range of from 3 to 10, more preferably from 5 to 9. With respect to the buffer used in the reaction system in the step (B) of the first embodiment, there is no particular limitation as long as the buffer is appropriately selected depending on the optimum pH value for the antigen-antibody reaction. For example, one or more buffers selected from the group consisting of a Tris buffer, a phosphate buffer, an acetic acid buffer and a Good's buffer can be used. If desired, a salt, such as NaCl and KCl, and an SH group-containing protective reagent, such as dithiothreitol, dithioerythritol and glutathione, may be added to the buffer in the reaction system. Further, depending on the type of the material of a container for accommodating the reaction system therein, a protein (such as albumin and IgG), an amino acid or a polyamino acid (such as lysine and poly-L-lysine) and a surfactant may be added to the reaction system as an adsorption preventive agent for preventing the components of the reaction system from being adsorbed on the inner wall of the container. For stabilizing the nucleic acid immobilized on the solid phase, ethylene glycol and a ribonuclease inhibitor may be added to the reaction system.

With respect to the reaction time in the step (B) of the first embodiment, there is no particular limitation as long as the antigen-antibody reaction of the reverse transcriptase activity-inhibiting antibody is performed to an extent such that the bound antibody can be detected. However, it is preferred that the reaction time of the step (B) is in the range of from 1 second to 24 hours.

With respect to the reaction conditions for the reverse transcriptase reaction in the step (C) of the first embodiment, there is no particular limitation as long as the reverse transcriptase reaction can proceed. For example, with respect to the pH value of the reaction system in the step (C) of the first embodiment, there is no particular limitation as long as the pH is adjusted to an optimum pH value for the reverse transcriptase reaction. It is preferred that the pH value of the reaction system is in the range of from 3 to 10, more preferably from 5 to 9. With respect to the buffer used in the reaction system in the step (C) of the first embodiment, there is no particular limitation as long as the buffer is appropriately selected depending on the adjusted pH value for the reverse transcriptase reaction. For example, one or more buffers selected from the group consisting of a Tris buffer, a phosphate buffer, an acetic acid buffer and a Good's buffer can be used. If desired, a salt, such as NaCl and KCl, and an SH group-containing protective reagent, such as dithiothreitol, dithioerythritol and glutathione, may be added to the buffer in the reaction system. Further, depending on the type of the material of a container for accommodating the reaction system therein, a protein (such as albumin and IgG), an amino acid or a polyamino acid (such as lysine and poly-L-lysine) and a surfactant may be added to the reaction system as an adsorption preventive agent for preventing the components of the reaction system from being adsorbed on the inner wall of the container. For stabilizing the nucleic acid immobilized on the solid phase, ethylene glycol and a ribonuclease inhibitor may be added to the reaction system.

Hereinbelow, the second embodiment of the present invention will be described in detail.

In the second embodiment of the present invention, with respect to the solid phase carrier, the method for immobilizing a nucleic acid on the solid phase, the oligo dT and poly A to be immobilized on the solid phase, the reverse transcriptase, the biological sample and the deoxymononucleotide triphosphate, those which are mentioned above in connection with the first embodiment may be employed.

In the step (E) of the second embodiment, the antigen-antibody reaction of a reverse transcriptase with a reverse transcriptase activity-inhibiting antibody is conducted. This step of the second embodiment corresponds to the step (B) of the first embodiment. Therefore, with respect to the reaction conditions for step (E), it is preferred that the same reaction conditions as in the step (B) of the first embodiment are employed.

In the step (F) of the second embodiment, the binding of the reverse transcriptase to a template-primer is conducted. This step of the second embodiment corresponds to the step (A) of the first embodiment. Therefore, with respect to the reaction conditions for step (F), it is preferred that the same reaction conditions as in the step (A) of the first embodiment are employed. Further, with respect to the reaction conditions for step (F), it is preferred that the binding of the reverse transcriptase to the template-primer is conducted in the presence of a water-soluble metal salt capable of producing bivalent metal ions; however, the reaction conditions are not limited to this. In addition, with respect to the type of metal ions, the concentration of the metal ions, the pH value of the reaction system, the reaction temperature, the reaction time and various components preferably used in the reaction system, those which are mentioned above in connection with the step (A) of the first embodiment are preferably employed in the step (F) of the second embodiment.

Further, with respect to the components used in the step (F) of the second embodiment, it is possible that the components are added, in advance, to the reaction system of step (E) of the second embodiment in which step (E) the antigen-antibody reaction of the antibody with the reverse transcriptase is performed, and the resultant reaction mixture is directly used in the step (F). It is also possible that the components are added to the reaction mixture of step (E) after completion of the antigen-antibody reaction and the resultant mixture is used in the step (F).

In the step (G) of the second embodiment, a reverse transcriptase reaction is conducted. This step of the second embodiment corresponds to the step (C) of the first embodiment. Therefore, with respect to the reaction conditions of step (G), it is preferred to use the same reaction conditions as in the step (C) of the first embodiment.

Hereinbelow, the third embodiment of the present invention is described below.

In the third embodiment of the present invention, with respect to the solid phase carrier, the method for immobilizing the nucleic acid on the solid phase, the oligo dT and poly A to be immobilized on the solid phase, the reverse transcriptase, the biological sample and the deoxymononucleotide triphosphate, those which are mentioned above in connection with the first embodiment may be employed.

In the step (I) of the third embodiment, the binding of a reverse transcriptase to a template-primer is conducted. This step of the third embodiment corresponds to the step (A) of the first embodiment and the step (F) of the second embodiment. Therefore, with respect to the reaction conditions of step (I), it is preferred that the same reaction conditions as in the step (A) of the first embodiment are employed. Further, in the step (I), it is preferred that the binding of the reverse transcriptase to the template-primer is conducted in the presence of a water-soluble metal salt capable of producing bivalent metal ions. With respect to the type of metal ions, the concentration of the metal ions, the pH value of the reaction system, the reaction temperature, the reaction time, and various components preferably used in the reaction system, those which are mentioned above in connection with the step (A) of the first embodiment are preferably employed in the step (I) of the third embodiment.

In the step (J) of the third embodiment, both a reverse transcriptase reaction and an antigen-antibody reaction of the reverse transcriptase with the reverse transcriptase activity-inhibiting antibody are conducted. This step (J) of the third embodiment corresponds to the steps (B) and (C) of the first embodiment, and also to the steps (E) and (G) of the second embodiment. With respect to the reaction conditions of step (J), there is no particular limitation as long as the reverse transcriptase reaction can be detected, and the substrate for the DNA synthesis, such as $^{3}$H-dTTP, $^{32}$P-dTTP or biotinylated dUTP, is added to the reaction system, under the same reaction conditions as in the step (B), in a concentration such that the reverse transcriptase activity can be detected. Further, there is no particular limitation as long as the reaction components generally used in an antigen-antibody reaction are contained in a reaction system for the step (J), which is used under the same reaction conditions as in step (C) of the first embodiment. As examples of components used in the reaction system, there can be mentioned a buffer for adjusting the pH value to an optimum pH value for an antibody-antigen reaction. For example, one or more buffers selected from the group consisting of a Tris buffer, a phosphate buffer, an acetic acid buffer and a Good's buffer can be used. If desired, a salt, such as NaCl and KCl, and an SH group-containing protective reagent, such as dithiothreitol, dithioerythritol and glutathione, may be added to the buffer in the reaction system. Further, depending on the type of the material of a container for accommodating the reaction system therein, a protein (such as albumin and IgG), an amino acid or a polyamino acid (such as lysine and poly-L-lysine) and a surfactant may be added to the reaction system as an adsorption preventive agent for preventing the components of the reaction system from being adsorbed on the inner wall of the container. For stabilizing the nucleic acid immobilized on the solid phase, ethylene glycol and a ribonuclease inhibitor may be added to the reaction system.

In each of the step (D) of the first embodiment, the step (H) of the second embodiment and the step (K) of the third embodiment, with respect to the methods for detecting the deoxyribonucleic acid synthesized on the solid phase by the reverse transcriptase reaction, a radioisotope labeled substrate, such as $^3$H-dTTP or $^{32}$P-dTTP, may be used as a substrate for the reverse transcriptase reaction. When a radioisotope labeled substrate is used, the unreacted substrate is removed from the reaction system by washing after completion of the reverse transcriptase reaction and then, the residual radioactivity on the solid phase may be measured. In addition, as a substrate for the reverse transcriptase reaction, a non-radioisotope labeled substrate, such as biotinylated dUTP, may be used. When a non-radioisotope labeled substrate is used, the unreacted substrate is removed from the reaction system by washing after completion of the reverse transcriptase reaction and then, the resultant material is reacted with avidin or streptoavidin which is labeled by a peroxidase or an alkaline phosphatase, followed by removal of the unreacted substrate by washing, whereupon the residual activity of the peroxidase or alkaline phosphatase on the solid phase is measured. The above-mentioned methods (Nakano et al. described in "Kansenshou-gaku Zasshi (The Journal of the Japanese Association for Infectious Diseases), vol. 68, No. 7, 923–931 (1994), Japan") are widely employed.

With respect to the above-mentioned three embodiments, more illustrative explanation is made below. As mentioned in connection with the "group 1" above, the first embodiment is a method for determining a group of antibodies having the ability to inhibit a DNA-chain elongation by an irreversible binding of the antibody (contained in a biological sample) to the reverse transcriptase. In the first embodiment, for example, the reverse transcriptase is dissolved in a 50 mM magnesium chloride solution and then, the resultant solution is added to the wells of a 96-well plate for EIA on which oligo dT·poly A is immobilized as a template-primer, followed by incubation at 37° C. for 1 hour, to thereby bind the reverse transcriptase to the template-primer. Then, the reverse transcriptase remaining unreacted is removed from the plate by washing, and to the plate is added a test sample which is obtained by diluting a biological sample containing a reverse transcriptase activity-inhibiting antibody with a 1% Triton X-100 solution or the like, followed by incubation at 37° C. for 1 hour. Subsequently, the antibody remaining unreacted is removed from the plate by washing, and to the plate is added a solution containing the substrates for the reverse transcriptase reaction including biotinylated dUTP, followed by incubation at 37° C. for 2 hours. Then, the substrate remaining unreacted is removed from the plate by washing, and to the plate is added alkaline phosphatase-labeled streptoavidin, followed by incubation at 37° C. for 1 hour. Then, all reactants remaining unreacted are removed by washing and then, to the plate is added para-nitrophenyl phosphate which is a substrate for an alkaline phosphatase, followed by incubation at 37° C. for 30 minutes, to thereby develop a color. With respect to the biotinylated DNA in the resultant plate, an absorbance at 405 nm is measured by means of a plate reader. The antibody can be quantitatively determined with ease by determining the residual reverse transcriptase activity (%) observed in the presence of a test sample, relative to the reverse transcriptase activity (100%) determined using a 1% Triton X-100 solution (i.e. not containing the biological sample) used for diluting the biological sample.

As mentioned in connection with the "group 2" above, the second embodiment is a method for determining a group of antibodies having the ability to inhibit the binding of a reverse transcriptase to a template-primer. In the second embodiment, for example, first, a mixture of the reverse transcriptase derived from HIV and a biological sample containing a reverse transcriptase activity-inhibiting antibody is prepared so that the reaction mixture contains 50 mM HEPES buffer (pH 7.5) and 150 mM sodium chloride, followed by incubation at 37° C. for 1 hour, to thereby allow an antigen-antibody reaction between the reverse transcriptase and the antibody. To the resultant reaction mixture is added magnesium chloride so that the concentration of magnesium chloride in the reaction system is 50 mM, and then, the resultant material is added to the wells of a 96-well plate for EIA on which oligo dT·poly A is immobilized as a template-primer. An incubation at 37° C. for 1 hour is conducted to thereby bind the reverse transcriptase to the template-primer. Then, the reverse transcriptase remaining unreacted is removed from the plate by washing. Then, to the plate is added a solution containing the substrates for the reverse transcriptase reaction including biotinylated dUTP, followed by incubation at 37° C. for 2 hours. The antibody can be quantitatively determined with ease by detecting the deoxyribonucleic acid synthesized on the solid phase in accordance with the same method for detecting the antibody as described in connection with the "group 1" above.

As mentioned in connection with "group 3" above, the third embodiment is a method for determining a group of antibodies having the ability to inhibit a DNA-chain elongation by the binding of an antibody (contained in a biological sample) to a reverse transcriptase which is synthesizing a DNA. In the third embodiment, for example, the reverse transcriptase derived from HIV is dissolved in a 50 mM magnesium chloride solution and then, the resultant solution is added to the wells of a 96-well plate for EIA on which oligo dT·poly A is immobilized as a template-primer, followed by incubation at 37° C. for 1 hour, to thereby bind the reverse transcriptase to the template-primer. Then, the reverse transcriptase remaining unreacted is removed from the plate by washing, and to the plate are added both a test sample which is obtained by diluting a biological sample containing a reverse transcriptase activity-inhibiting antibody with a 1% Triton X-100 or the like, and a solution containing a substrate solution for the reverse transcriptase reaction including biotinylated dUTP, followed by reverse transcriptase reaction at 37° C. for 2 hours. Then, the substrate remaining unreacted is removed from the plate by washing. The antibody can be quantitatively determined with ease by detecting the deoxyribonucleic acid synthesized on the solid phase in accordance with the same method for detecting the antibody as described in connection with the "group 1" above.

As mentioned above, the present invention provides an easy and highly reproducible method for classifying and quantitatively determining the antibodies against the epitopes of a viral reverse transcriptase. Using the method of the present invention, not only the virus which has mutated during a latent period thereof, and the properties which the virus exhibits as a result of the mutation, but also a virus which has acquired drug resistance as a result of the administration of the drugs to the host, can be studied by quantitatively determining the antibodies. Further, it has also become possible to accurately and promptly determine the changes in the infected host, such as the change in the ability to produce antibodies, which occur in accordance with the progression of illness. In addition, the method of the present invention is advantageous in that the biological samples used are easily available, and that cumbersome procedures, such as culturing of the virus, is not required. Therefore, the method of the present invention is effective for the diagnosis and the like of HIV which necessarily include testings for an extremely large number of test items. Further, the method of the present invention can be advantageously used for the study of HIV infection because an antibody is more stable than a viral antigen and a high biosafety can be achieved by the treatment of the biological samples with a surfactant.

BEST MODE FOR CARRYING OUT THE INVENTION

Hereinbelow, the present invention will be described in more detail with reference to the following Examples, which should not be construed as limiting the scope of the present invention.

EXAMPLE 1

(1) Preparation of an oligo dT·poly A-immobilized plate

Oligo $dT_{19-24}$ (average chain length: 22 nucleotides) (manufactured and sold by Sigma Chemical Company, U.S.A) was dissolved in an aqueous solution containing 100 mM l-ethyl-3-(3-dimethyl aminopropyl)carbodiimide chloride (hereinafter, frequently referred to simply as "CDI") (manufactured and sold by Peptide Institute Inc., Japan) and 100 mM 1-methylimidazole-HCl buffer (pH 7.0; hereinafter, frequently referred to simply as "IMD") (manufactured and sold by Sigma Chemical Company, U.S.A), thereby obtaining a solution containing oligo $dT_{19-24}$ in a concentration of 200 ng/100 μl. 100 μl of the obtained solution was placed in each well of a 96-well amino plate (manufactured and sold by Sumitomo Bakelite Co., Ltd., Japan) and then, a reaction was allowed to proceed at room temperature for 24 hours, to thereby immobilize oligo $dT_{19-24}$ on the plate. Subsequently, the reaction solution was discarded from the wells and then, the wells were washed three times with 200 μl of 0.1M Tris-HCl buffer containing 0.15M sodium chloride (pH 7.5; hereinafter, frequently referred to simply as "TBS"). Poly A (manufactured and sold by Pharmacia Fine Chemicals AB, Sweden) was dissolved in 80 mM Tris-HCl buffer (pH 7.5) containing 0.6M sodium chloride, 4 mM disodium ethylenediaminetetraacetate and 0.1% sodium dodecyl sulfate, thereby obtaining a solution containing poly A in a concentration of 10 μg/100 μl. 100 μl of the obtained solution was placed in each of the wells of the plate on which the oligo dT was immobilized, followed by incubation at 37° C. for 16 hours. Subsequently, the solution in each of the wells was discarded and then, each of the wells was washed with TBS three times, to thereby prepare an oligo dT·poly A-immobilized plate.

(2) Binding of a reverse transcriptase to the oligo dT·poly A immobilized on the plate Individually prepared were six different types of solutions which respectively contained magnesium chloride in concentrations of 0.01, 0.1, 1, 10, 100 and 1,000 mM and each of which contained 0.1% Triton X-100 and 0.1 mU/100 μl HIV-1 reverse transcriptase (expression product obtained by means of recombinant *Escherichia coli*) (manufactured and sold by SEIKAGAKU KOGYO CO., LTD, Japan). 100 μl of each of the prepared solutions was individually placed in each well of the oligo dT·poly A-immobilized plate prepared in item (1) above, followed by incubation at 37° C. for 1 hour. After the incubation, the wells were washed five times with a TBS solution containing 0.02% polyoxyethylene (20) sorbitan monolaurate, to thereby prepare a reverse transcriptase-bound plate.

(3) Reaction of a test sample with the reverse transcriptase-bound plate

Sera were respectively sampled from five hemophiliacs infected with HIV and five persons free from HIV infection. Each of the sampled sera was diluted 200-fold with 10 mM phosphate buffer (pH 7.4), containing 150 mM sodium chloride and 0.1% Triton X-100, to thereby obtain test samples. 100 μl of each of the obtained test samples was individually placed in each well of the reverse transcriptase-bound plate as prepared in item (2) above, followed by incubation at 37° C. for 1 hour. After the incubation, the solution in each of the wells of the plate was discarded and then, each of the wells was washed five times with a TBS solution containing 0.02% polyoxyethylene (20) sorbitan monolaurate.

On the other hand, a control was prepared in substantially the same manner as described above, except that, instead of the test sample prepared above, 100 μl of a solution containing 10 mM phosphate buffer solution (pH 7.4), 150 mM sodium chloride and 0.1% Triton X-100 was placed in each well of the reverse transcriptase-bound plate as prepared in item (2) above.

(4) Detection of reverse transcriptase activity

100 μl of an aqueous solution, which contained 90 mM HEPES (pH 7.8), 126 mM potassium chloride, 9 mM magnesium chloride, 0.45 mM dithiothreitol, 1.08 mM reduced glutathione, 1% Triton X-100, 1.8% ethylene glycol, 117 μM deoxythymidine triphosphate (dTTP) and 3 μM biotinylated deoxyuridine triphosphate (Bio-dUTP; manufactured and sold by Boehringer-Mannheim GmbH, Germany), was placed in each well of the reverse transcriptase-bound plate and reacted with a test sample, to thereby perform a reverse transcriptase reaction at 37° C. for 2 hours. Using the control prepared in item (3) above, substantially the same procedure as mentioned above was conducted.

After performing the reaction, 10 μl of a 5M sodium chloride solution was placed in each well of the plate and then, the plate was allowed to stand at room temperature for 5 minutes. Then, the solution in each of the wells was discarded, followed by washing of each of the wells five times with a TBS solution containing 0.02% polyoxyethylene (20) sorbitan monolaurate. 100 μl of a 20,000-fold dilution of alkaline phosphatase labeled-streptoavidin (manufactured and sold by Jackson Immuno Research Laboratory Co., U.S.A.), prepared using 50 mM Tris-HCl buffer (pH 7.5) containing 0.5M sodium chloride, 5 mM magnesium chloride and 2% bovine serum albumin, was placed in each well of the plate, followed by incubation at 37° C. for 1 hour. Then, the wells of the plate were washed five times with a TBS solution containing 0.02% polyoxyethylene (20) sorbitan monolaurate.

After washing the wells, 150 μl of a diethanolamine-HCl buffer (pH 9.5) containing 1 mM magnesium chloride and 1 mg/ml para-nitrophenyl phosphate disodium (manufactured and sold by Sigma Chemical Company, U.S.A) was placed in each of the wells, followed by incubation at 37° C. for 30 minutes. Subsequently, 50 μl of a 1N aqueous sodium hydroxide solution was added to the wells to thereby detect the biotinylated DNA which is a product of the reverse transcriptase reaction. With respect to each of the biotinylated DNA, an absorbance value at 405 nm was measured by means of a plate reader.

(5) Quantitative determination of the antibody having the ability to inhibit the activity of the reverse transcriptase Using the absorbance values obtained in item (4) above, each of the absorbance values obtained from the reverse transcriptase reacted with the test sample was divided by the absorbance value obtained from the control reverse transcriptase (not reacted with the test sample). The residual activity of reverse transcriptase (%) after the reaction with the test sample was calculated, relative to the control reverse transcriptase activity (100%). Results are shown in Table 1.

immobilized on the plate" mentioned in item (2) above. With respect to the test samples prepared using the sera of the HIV-infected persons, the residual activities of the reverse transcriptase were 56% for H. K., 63% for K. K. and 71% for K. S., whereas with respect to the test samples prepared using the sera of the HIV-uninfected persons, the residual activities of the reverse transcriptase were 103.4% for M. T., 100.3% for T. E. and 110.4% for T. T.

EXAMPLE 2

By substantially the same procedure as in the "preparation of an oligo dT·poly A-immobilized plate" mentioned in item (1) above in Example 1, an oligo dT·poly A-immobilized plate was prepared. Using the prepared oligo dT·poly A-immobilized plate, substantially the same procedure as in the "binding of a reverse transcriptase to the oligo dT·poly A immobilized on the plate" mentioned in item (2) above in Example 1 was repeated, except that, instead of magnesium chloride, each of manganese chloride and calcium chloride was individually used, to thereby prepare reverse

TABLE 1

| Magnesium | Residual activity of reverse transcriptase (%) | | | | | | | | | |
|---|---|---|---|---|---|---|---|---|---|---|
| concentration | HIV-positive person | | | | | HIV-negative person | | | | |
| (mM) | F.O. | Y.U. | S.T. | K.A. | Y.K. | I.K. | R.Y. | K.Y. | T.K. | T.I. |
| 0.01 | 43.2 | 23.4 | 35.4 | 59.2 | 82.1 | 101.4 | 104.3 | 105.3 | 102.0 | 103.3 |
| 0.1 | 44.1 | 19.2 | 31.3 | 59.0 | 83.1 | 100.3 | 99.9 | 102.2 | 105.3 | 103.4 |
| 1 | 48.2 | 22.2 | 34.1 | 56.3 | 86.8 | 102.3 | 105.9 | 101.7 | 106.2 | 104.8 |
| 10 | 45.0 | 27.4 | 34.7 | 52.4 | 85.6 | 99.7 | 102.5 | 103.4 | 108.2 | 102.2 |
| 100 | 49.9 | 29.3 | 35.8 | 58.8 | 89.1 | 106.2 | 100.0 | 102.3 | 106.1 | 108.0 |
| 1,000 | 48.4 | 26.5 | 35.4 | 59.1 | 86.7 | 100.3 | 106.5 | 105.6 | 107.2 | 102.1 |

*Each combination of two letters in the above table individually represents the initials of the person who offered serum for testing.

As shown in Table 1, the antibodies, which were irreversibly bound to the reverse transcriptase to thereby inhibit the chain elongation of a complementary DNA to the RNA template, were individually, quantitatively determined with respect to the residual enzyme activity of the reverse transcriptase. The antibodies could be detected in any magnesium ion concentrations indicated in Table 1.

Further, the quantitative determination of the antibodies was separately conducted using the plate prepared using a solution containing 0 mM magnesium chloride, 0.1% Triton X-100 and 5 mU/100 μl reverse transcriptase in the "binding reaction of the reverse transcriptase to the oligo dT·poly A transcriptase-bound plates. Then, substantially the same procedure as in the "reaction of a test sample with the reverse transcriptase-bound plate" mentioned in item (3) above in Example 1, the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 2, were used. Results are shown in Table 2.

TABLE 2

| | Residual activity of reverse transcriptase (%) | | | | | | | | | |
|---|---|---|---|---|---|---|---|---|---|---|
| | HIV-positive person | | | | | HIV-negative person | | | | |
| | F.O. | Y.U. | S.T. | K.A. | Y.K. | I.K. | R.Y. | K.Y. | T.K. | T.I. |
| Manganese concentration (mM) | | | | | | | | | | |
| 0.01 | 44.2 | 23.5 | 38.9 | 69.2 | 72.4 | 111.2 | 102.3 | 104.2 | 112.8 | 103.5 |
| 0.1 | 44.4 | 29.2 | 37.2 | 61.0 | 73.3 | 105.4 | 109.9 | 101.3 | 125.3 | 101.9 |
| 1 | 46.9 | 26.6 | 37.1 | 63.8 | 75.9 | 102.6 | 115.5 | 106.4 | 116.5 | 109.9 |
| 10 | 42.0 | 28.1 | 36.8 | 62.4 | 72.0 | 109.4 | 107.5 | 109.8 | 114.0 | 102.2 |
| 100 | 46.9 | 28.1 | 31.8 | 58.2 | 79.1 | 110.9 | 101.0 | 102.2 | 106.1 | 105.0 |
| 1,000 | 43.3 | 25.4 | 29.4 | 59.9 | 76.4 | 103.2 | 104.6 | 105.3 | 117.4 | 112.7 |

TABLE 2-continued

| | Residual activity of reverse transcriptase (%) | | | | | | | | | |
|---|---|---|---|---|---|---|---|---|---|---|
| | HIV-positive person | | | | | HIV-negative person | | | | |
| | F.O. | Y.U. | S.T. | K.A. | Y.K. | I.K. | R.Y. | K.Y. | T.K. | T.I. |
| Calcium concentration (mM) | | | | | | | | | | |
| 0.01 | 34.5 | 26.3 | 32.4 | 69.5 | 92.6 | 111.1 | 105.6 | 125.3 | 114.4 | 104.3 |
| 0.1 | 33.1 | 29.5 | 34.6 | 71.4 | 93.7 | 106.9 | 100.9 | 125.2 | 126.2 | 107.4 |
| 1 | 38.7 | 21.8 | 39.1 | 68.2 | 96.3 | 107.0 | 115.0 | 127.7 | 113.1 | 111.8 |
| 10 | 34.4 | 20.9 | 35.7 | 68.6 | 85.5 | 109.5 | 113.4 | 112.4 | 105.8 | 101.6 |
| 100 | 39.0 | 19.1 | 37.4 | 62.9 | 89.9 | 116.2 | 105.5 | 128.3 | 119.6 | 104.6 |
| 1,000 | 33.3 | 25.2 | 39.7 | 69.4 | 86.9 | 113.2 | 104.4 | 125.3 | 127.4 | 112.5 |

*Each combination of two letters in the above table individually represents the initials of the person who offered serum for testing.

As shown in Table 2, the antibodies, which were irreversibly bound to the reverse transcriptase to thereby inhibit the chain elongation of a complementary DNA to the RNA template, were individually, quantitatively determined with respect to the residual enzyme activity of the reverse transcriptase. The antibodies could be detected in the presence of any metal ions and in any metal ion concentration indicated in Table 2.

EXAMPLE 3

Oligo dT·poly A-immobilized plates were prepared by substantially the same procedure as in the "preparation of an oligo dT·poly A-immobilized plate" mentioned in item (1) above in Example 1, except that, instead of the oligo $dT_{19-24}$, each of oligo $dT_5$, oligo $dT_{10}$ (manufactured and sold by Sigma Chemical Company, U.S.A), oligo $dT_{25-30}$ and poly dT (average chain length: 794 nucleotides) (manufactured and sold by Pharmacia Fine Chemicals AB, Sweden) was individually used. Using the prepared oligo dT·poly A-immobilized plates, substantially the same procedure as in the "binding of a reverse transcriptase to the oligo dT·poly A immobilized on the plate" mentioned in item (2) above in Example 1 was repeated, except that the concentration of magnesium chloride was 50 mM, to thereby prepare reverse transcriptase-bound plates. Then, substantially the same procedure as in the "reaction of a test sample with the reverse transcriptase-bound plate" mentioned in item (3) above in Example 1, the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 3, were used. Results are shown in Table 3.

TABLE 3

| | Residual activity of reverse transcriptase (%) | | | | | | | | | |
|---|---|---|---|---|---|---|---|---|---|---|
| Type of | HIV-positive person | | | | | HIV-negative person | | | | |
| oligo dT | H.M. | T.A. | J.O. | S.S. | T.M. | I.K. | R.Y. | K.Y. | T.K. | T.I. |
| Oligo $dT_5$ | 12.2 | 65.4 | 57.7 | 85.9 | 23.5 | 110.3 | 131.2 | 108.3 | 110.0 | 108.6 |
| Oligo $dT_{10}$ | 15.3 | 63.4 | 60.1 | 79.9 | 20.0 | 105.2 | 125.3 | 110.2 | 116.7 | 111.0 |
| Oligo $dT_{25-30}$ | 11.6 | 62.5 | 61.3 | 82.4 | 19.9 | 102.3 | 113.2 | 104.9 | 110.1 | 100.2 |
| Poly dT | 18.5 | 71.1 | 58.1 | 80.3 | 24.5 | 110.3 | 111.5 | 109.4 | 111.2 | 120.5 |

*Each combination of two letters in the above table individually represents the initials of the person who offered serum for testing.

As shown in Table 3, the antibodies, which were irreversibly bound to the reverse transcriptase to thereby inhibit the chain elongation of a complementary DNA to the RNA template, were individually, quantitatively determined with respect to the residual enzyme activity of the reverse transcriptase. The antibodies could be detected in any oligo dT length indicated in Table 3.

EXAMPLE 4

Oligo dT·poly A-immobilized plates were prepared by substantially the same procedure as in the "preparation of an oligo dT·poly A-immobilized plate" mentioned in item (1) above in Example 1, except that, instead of the poly A, each of oligo $A_{12-18}$ and poly A (average chain length: 534 nucleotides) (manufactured and sold by Pharmacia Fine Chemicals AB, Sweden) was individually used. Using the prepared oligo dT·poly A-immobilized plates, substantially the same procedure as in the "binding of a reverse transcriptase to the oligo dT·poly A immobilized on the plate" mentioned in item (2) above in Example 1 was repeated, except that the concentration of magnesium chloride was 50 mM, to thereby prepare reverse transcriptase-bound plates. Then, substantially the same procedure as in the "reaction of a test sample with the reverse transcriptase-bound plate" mentioned in item (3) above in Example 1, the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 4, were used. Results are shown in Table 4.

TABLE 4

| Type of poly A | Residual activity of reverse transcriptase (%) | | | | | | | | | |
|---|---|---|---|---|---|---|---|---|---|---|
| | HIV-positive person | | | | | HIV-negative person | | | | |
| | H.M. | T.A. | J.O. | S.S. | T.M. | I.K. | R.Y. | K.Y. | T.K. | T.I. |
| Oligo $A_{12-18}$ | 18.5 | 74.5 | 55.5 | 73.3 | 42.1 | 110.1 | 122.2 | 121.2 | 130.0 | 114.2 |
| Poly A | 18.1 | 68.6 | 59.3 | 71.2 | 40.6 | 115.2 | 125.4 | 120.7 | 121.5 | 119.8 |

*Each combination of two letters in the above table individually represents the initials of the person who offered serum for testing.

As shown in Table 4, the antibodies, which were irreversibly bound to the reverse transcriptase to thereby inhibit the chain elongation of a complementary DNA to the RNA template, were individually, quantitatively determined with respect to the residual enzyme activity of the reverse transcriptase. The antibodies could be detected in any poly A length indicated in Table 4.

EXAMPLE 5

By substantially the same procedure as in the "preparation of an oligo dT·poly A-immobilized plate" mentioned in item (1) above in Example 1, an oligo dT·poly A-immobilized plate was prepared. Using the prepared oligo dT·poly A-immobilized plate, substantially the same procedure as in the "binding of a reverse transcriptase to the oligo dT·poly A immobilized on the plate" mentioned in item (2) above in Example 1 was repeated, except that the concentration of magnesium chloride was 50 mM, and each of 0.1, 1, 10, 100, 1,000, 10,000 and 100,000 mU/100 μl reverse transcriptases was individually used, to thereby prepare reverse transcriptase-bound plates. Then, substantially the same procedure as in the "reaction of a test sample with the reverse transcriptase-bound plate" mentioned in item (3) above in Example 1, the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 5, were used.

On the other hand, substantially the same procedure as mentioned above was repeated, except that 0.1, 1 and 10 μU/100 μl HIV-1 reverse transcriptases were individually used, and that, instead of 2 hours, a reverse transcriptase reaction was performed for 24 hours. Results are shown in Table 5.

TABLE 5

| Amount of reverse transcriptase | Residual activity of reverse transcriptase (%) Samples | | | | |
|---|---|---|---|---|---|
| | M.S. | H.H. | N.T. | Y.I. | Y.Y. |
| (μU/100 μl) | | | | | |
| 0.1 | 0.2 | 0.3 | 0.1 | 0.1 | 0.2 |
| 1 | 1.1 | 0.3 | 0.2 | 0.1 | 0.3 |
| 10 | 0.9 | 0.5 | 0.3 | 0.1 | 0.6 |

TABLE 5-continued

| Amount of reverse transcriptase | Residual activity of reverse transcriptase (%) Samples | | | | |
|---|---|---|---|---|---|
| | M.S. | H.H. | N.T. | Y.I. | Y.Y. |
| (mU/100 μl) | | | | | |
| 0.1 | 5.3 | 3.1 | 1.2 | 2.2 | 4.9 |
| 1 | 11.1 | 7.4 | 5.1 | 6.8 | 10.2 |
| 10 | 35.4 | 21.2 | 12.2 | 10.0 | 25.4 |
| 100 | 49.3 | 41.2 | 34.2 | 18.1 | 43.3 |
| 1,000 | 71.6 | 68.7 | 52.2 | 48.4 | 73.9 |
| 10,000 | 90.9 | 86.9 | 74.2 | 75.3 | 91.2 |
| 100,000 | 98.3 | 95.2 | 84.3 | 88.8 | 96.8 |

*Each combination of two letters in the above table individually represents the initials of the person who offered serum for testing.

As shown in Table 5, the antibodies, which were irreversibly bound to the reverse transcriptase to thereby inhibit the chain elongation of a complementary DNA to the RNA template, were individually, quantitatively determined with respect to the residual enzyme activity of the reverse transcriptase. The antibodies could be detected in any reverse transcriptase concentrations indicated in Table 5.

EXAMPLE 6

By substantially the same procedure as in the "preparation of an oligo dT·poly A-immobilized plate" mentioned in item (1) above in Example 1, an oligo dT·poly A-immobilized plate was prepared. Using the prepared oligo dT·poly A-immobilized plate, substantially the same procedure as in the "binding of a reverse transcriptase to the oligo dT·poly A immobilized on the plate" mentioned in item (2) above in Example 1 was repeated, except that the concentration of magnesium chloride was 50 mM, to thereby prepare a reverse transcriptase-bound plate. Using the prepared reverse transcriptase-bound plate, substantially the same procedure as in the "reaction of a test sample with the reverse transcriptase-bound plate" mentioned in item (3) above in Example 1 was repeated, except that each of the sampled sera was individually diluted 1-fold, 10-fold, 100-fold, 1,000-fold, 10,000-fold and 100,000-fold. Then, substantially the same procedure as in the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 6, were used. Results are shown in Table 6.

TABLE 6

| Serum dilution ratio (fold) | Residual activity of reverse transcriptase (%) | | | | | | | | | |
|---|---|---|---|---|---|---|---|---|---|---|
| | HIV-positive person | | | | | HIV-negative person | | | | |
| | M.S. | H.H. | N.T. | Y.I. | Y.Y. | I.K. | R.Y. | K.Y. | T.K. | T.I. |
| 1 | 0.1 | 0.1 | 0.2 | 0.1 | 0.4 | 99.2 | 106.9 | 105.3 | 101.2 | 100.9 |
| 10 | 1.2 | 1.5 | 2.2 | 0.9 | 5.4 | 100.2 | 101.1 | 103.1 | 100.0 | 101.1 |
| 100 | 29.7 | 22.3 | 31.5 | 10.6 | 35.3 | 110.2 | 125.3 | 116.7 | 111.0 | 105.2 |
| 1,000 | 54.2 | 43.8 | 60.2 | 23.3 | 65.9 | 108.3 | 131.2 | 110.0 | 108.6 | 111.2 |
| 10,000 | 93.2 | 75.9 | 74.2 | 45.3 | 81.2 | 109.4 | 111.5 | 111.2 | 120.5 | 110.3 |
| 100,000 | 98.0 | 85.5 | 84.3 | 59.8 | 96.0 | 104.9 | 113.2 | 110.1 | 100.2 | 102.3 |

*Each combination of two letters in the above table individually represents the initials of the person who offered serum for testing.

As shown in Table 6, the antibodies, which were irreversibly bound to the reverse transcriptase to thereby inhibit the chain elongation of a complementary DNA to the RNA template, were individually, quantitatively determined with respect to the residual enzyme activity of the reverse transcriptase. The antibodies could be detected in any serum dilution ratio indicated in Table 6.

EXAMPLE 7

(6) Preparation of an oligo dT·poly A-immobilized plate

By substantially the same procedure as in the "preparation of an oligo dT·poly A-immobilized plate" mentioned in item (1) above in Example 1, an oligo dT·poly A-immobilized plate was prepared.

(7) Antigen-antibody reaction of a test sample with a reverse transcriptase

In six test tubes were individually prepared six different types of solutions which respectively contained magnesium chloride in concentrations of 0.02, 0.2, 2, 20, 200 and 2,000 mM and each of which contained 0.1% Triton X-100 and 0.2 mU/100 μl HIV-1 reverse transcriptase (expression product obtained by means of recombinant *Escherichia coli*) (manufactured and sold by SEIKAGAKU KOGYO CO., LTD, Japan), thereby obtaining reverse transcriptase solutions. Sera were respectively sampled from five hemophiliacs infected with HIV and five persons free from HIV infection. Each of the sampled sera was diluted 200-fold with 10 mM phosphate buffer (pH 7.4), containing 150 mM sodium chloride and 0.1% Triton X-100, to thereby obtain test samples. 200 μl of each of the obtained test samples and 200 μl of each of the obtained reverse transcriptase solutions were placed in each of six other test tubes, and an antigen-antibody reaction was conducted at 37° C. for 1 hour. On the other hand, a control was prepared in substantially the same manner as described above, except that, instead of the test samples prepared as described above (i.e., serum dilution solutions), 200 μl of a solution containing 10 mM phosphate buffer solution (pH 7.4), 150 mM sodium chloride and 0.1% Triton X-100 was used.

(8) Binding of a reverse transcriptase to the oligo dT·poly A immobilized on the plate After completion of the antigen-antibody reaction of item (7) above, 100 μl of each of the resultant reaction mixtures was individually placed in each well of the oligo dT·poly A-immobilized plate prepared in item (6) above, followed by incubation at 37° C. for 1 hour. After the incubation, the solution in each of the wells was discarded and then, each of the wells was washed five times with a TBS solution containing 0.02% polyoxyethylene (20) sorbitan monolaurate, to thereby prepare a reverse transcriptase-bound plate. Using the control prepared in item (7) above, substantially the same procedure as mentioned above was conducted. Then, substantially the same procedure as in the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 7, were used. Results are shown in Table 7.

TABLE 7

| Magnesium concentration (mM) | Residual activity of reverse transcriptase (%) | | | | | | | | | |
|---|---|---|---|---|---|---|---|---|---|---|
| | HIV-positive person | | | | | HIV-negative person | | | | |
| | F.O. | Y.U. | S.T. | K.A. | Y.K. | I.K. | R.Y. | K.Y. | T.K. | T.I. |
| 0.01 | 10.2 | 21.3 | 52.2 | 10.2 | 2.3 | 132.2 | 145.3 | 125.3 | 124.3 | 131.2 |
| 0.1 | 11.2 | 19.3 | 48.3 | 5.3 | 3.3 | 129.2 | 139.9 | 135.2 | 131.1 | 130.2 |
| 1 | 9.3 | 18.9 | 44.6 | 6.2 | 5.6 | 119.2 | 125.3 | 127.6 | 133.9 | 133.1 |
| 10 | 9.3 | 13.3 | 45.2 | 8.8 | 2.1 | 114.1 | 129.2 | 128.3 | 133.6 | 145.2 |
| 100 | 9.9 | 10.1 | 39.9 | 3.3 | 2.0 | 126.8 | 120.0 | 133.7 | 129.1 | 135.5 |
| 1,000 | 10.3 | 10.0 | 46.3 | 8.8 | 4.2 | 122.2 | 135.3 | 130.0 | 129.0 | 124.9 |

*Each combination of two letters in the above table individually represents the initials of the person who offered serum for testing.

As shown in Table 7, the antibodies, which were individually, irreversibly bound to the reverse transcriptase to thereby inhibit the binding of the reverse transcriptase to the template-primer (oligo dT·poly A), were individually, quantitatively determined with respect to the residual enzyme activity of the reverse transcriptase. The antibodies could be detected in any magnesium ion concentration indicated in Table 7.

Further, the quantitative determination of the antibodies was separately conducted using the reverse transcriptase solution containing 0 mM magnesium chloride and 5 mU/100 μl reverse transcriptase in the "antigen-antibody reaction of a test sample with a reverse transcriptase" mentioned in item (7) above. With respect to the test samples prepared using the sera of the HIV-infected persons, the residual activities of the reverse transcriptase were 23.2% for H. K., 54.4% for K. K. and 48.0% for K. S., whereas with respect to the test samples prepared using the sera of the HIV-uninfected persons, the residual activities of the reverse transcriptase were 111% for M. T., 104.8% for T. E. and 102.7% for T. T.

EXAMPLE 8

By substantially the same procedure as in the "preparation of an oligo dT·poly A-immobilized plate" mentioned in item (6) above in Example 7, an oligo dT·poly A-immobilized plate was prepared. Substantially the same procedure as in the "antigen-antibody reaction of a test sample with a reverse transcriptase" mentioned in item (7) above in Example 7 was repeated, except that, instead of magnesium chloride, each of manganese chloride and calcium chloride was individually used. Then, substantially the same procedure as in the "binding of a reverse transcriptase to the oligo dT·poly A immobilized on the plate" mentioned in item (8) above in Example 7, the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 8, were used. Results are shown in Table 8.

As shown in Table 8, the antibodies, which were individually, irreversibly bound to the reverse transcriptase to thereby inhibit the binding of the reverse transcriptase to the template-primer (oligo dT·poly A), were individually, quantitatively determined with respect to the residual enzyme activity of the reverse transcriptase. The antibodies could be detected in the presence of any metal ions and in any metal ion concentration indicated in Table 8.

EXAMPLE 9

Oligo dT·poly A-immobilized plates were prepared by substantially the same procedure as in the "preparation of an oligo dT·poly A-immobilized plate" mentioned in item (6) above in Example 7, except that instead of the oligo $dT_{9-24}$, each of oligo $dT_5$, oligo $dT_{10}$ (manufactured and sold by Sigma Chemical Company, U.S.A), oligo $dT_{25-30}$ and poly dT (average chain length: 794 nucleotides) (manufactured and sold by Pharmacia Fine Chemicals AB, Sweden) was individually used. Substantially the same procedure as in the "antigen-antibody reaction of a test sample with a reverse transcriptase" mentioned in item (7) above in Example 7 was repeated, except that the concentration of magnesium chloride was 50 mM. After the antigen-antibody reaction, 100 μl of each of the resultant reaction mixtures was individually placed in each well of the oligo dT·poly A-immobilized plate prepared as mentioned above, followed by incubation at 37° C. for 1 hour. After the incubation, the solution in each of the wells was discarded and then, each of the wells was washed five times with a TBS solution containing 0.02% polyoxyethylene (20) sorbitan monolaurate, to thereby prepare a reverse transcriptase-bound plate. Using a control prepared by substantially the same procedure as in item (7) above in Example 7, substantially the same procedure as mentioned above was conducted. Then, substantially the same procedure as in the "detection of reverse transcriptase activity" mentioned in item (4) above in Example 1 and the "quantitative determination of the antibody having the ability to inhibit the activity of the reverse transcriptase" mentioned in item (5)

TABLE 8

| | Residual activity of reverse transcriptase (%) | | | | | | | | | |
|---|---|---|---|---|---|---|---|---|---|---|
| | HIV-positive person | | | | | HIV-negative person | | | | |
| | F.O. | Y.U. | S.T. | K.A. | Y.K. | I.K. | R.Y. | K.Y. | T.K. | T.I. |
| Manganese concentration (mM) | | | | | | | | | | |
| 0.01 | 15.2 | 11.4 | 41.4 | 16.2 | 1.3 | 121.3 | 122.3 | 134.2 | 112.2 | 113.6 |
| 0.1 | 11.3 | 11.2 | 40.6 | 13.2 | 1.5 | 125.3 | 123.5 | 132.3 | 125.4 | 118.9 |
| 1 | 10.9 | 8.5 | 39.2 | 15.9 | 2.2 | 124.0 | 123.6 | 132.4 | 121.0 | 119.1 |
| 10 | 12.2 | 10.0 | 40.2 | 13.9 | 1.7 | 122.8 | 124.2 | 133.2 | 125.8 | 111.0 |
| 100 | 11.7 | 11.6 | 45.2 | 12.4 | 2.8 | 124.8 | 126.8 | 129.9 | 124.3 | 128.0 |
| 1,000 | 10.9 | 9.9 | 48.2 | 13.3 | 3.7 | 119.6 | 116.5 | 135.9 | 125.5 | 123.6 |
| Calcium concentration (mM) | | | | | | | | | | |
| 0.01 | 13.1 | 11.4 | 31.3 | 10.1 | 2.4 | 111.4 | 128.9 | 114.6 | 114.6 | 133.1 |
| 0.1 | 10.9 | 10.1 | 35.2 | 12.3 | 1.2 | 122.3 | 127.9 | 123.0 | 115.0 | 129.8 |
| 1 | 15.3 | 12.2 | 38.9 | 11.0 | 2.1 | 110.5 | 127.4 | 132.5 | 124.0 | 128.9 |
| 10 | 13.3 | 10.2 | 32.3 | 10.7 | 1.8 | 124.2 | 128.3 | 125.1 | 121.2 | 126.3 |
| 100 | 15.3 | 10.3 | 33.6 | 12.9 | 3.8 | 121.3 | 129.9 | 131.0 | 120.6 | 135.3 |
| 1,000 | 13.9 | 9.5 | 38.2 | 13.5 | 3.3 | 119.9 | 126.1 | 133.4 | 120.7 | 134.2 |

*Each combination of two letters in the above table individually represents the initials of the person who offered serum for testing.

above in Example 1 was repeated, except that the reverse transcriptase-bound plates and the control, both prepared in this Example 9, were used. Results are shown in Table 9.

above was conducted. Then, substantially the same procedure as in the "detection of reverse transcriptase activity" mentioned in item (4) above in Example 1 and the "quan-

TABLE 9

| Type of | Residual activity of reverse transcriptase (%) | | | | | | | | | |
|---|---|---|---|---|---|---|---|---|---|---|
| | HIV-positive person | | | | | HIV-negative person | | | | |
| oligo dT | H.M. | T.A. | J.O. | S.S. | T.M. | I.K. | R.Y. | K.Y. | T.K. | T.I. |
| Oligo dT$_5$ | 11.2 | 13.2 | 3.2 | 5.9 | 23.6 | 140.5 | 131.6 | 118.3 | 110.4 | 138.6 |
| Oligo dT$_{10}$ | 10.3 | 13.2 | 1.5 | 6.9 | 21.2 | 135.3 | 131.1 | 121.2 | 115.3 | 137.2 |
| Oligo dT$_{25-30}$ | 8.9 | 11.0 | 2.2 | 5.6 | 19.3 | 135.3 | 130.9 | 121.7 | 117.9 | 129.2 |
| Poly dT | 10.2 | 10.0 | 3.3 | 5.2 | 22.7 | 140.1 | 132.2 | 124.3 | 116.2 | 137.7 |

*Each combination of two letters in the above table individually represents the initials of the person who offered serum for testing.

As shown in Table 9, the antibodies, which were individually, irreversibly bound to the reverse transcriptase to thereby inhibit the binding of the reverse transcriptase to the template-primer (oligo dT·poly A), were individually, quantitatively determined with respect to the residual enzyme activity of the reverse transcriptase. The antibodies could be detected in any oligo dT length indicated in Table 9.

EXAMPLE 10

Oligo dT·poly A-immobilized plates were prepared by substantially the same procedure as in the "preparation of an oligo dT·poly A-immobilized plate" mentioned in item (6) above in Example 7, except that, instead of the poly A, each of oligo A$_{12-18}$ and poly A (average chain length: 534 nucleotides) (manufactured and sold by Pharmacia Fine Chemicals AB, Sweden) was individually used. Substantially the same procedure as in the "antigen-antibody reaction of a test sample with a reverse transcriptase" mentioned in item (7) above in Example 7 was repeated, except that the concentration of magnesium chloride was 50 mM. After the antigen-antibody reaction, 100 µl of each of the resultant reaction mixtures was individually placed in each well of the oligo dT·poly A-immobilized plate prepared as mentioned above, followed by incubation at 37° C. for 1 hour. After the incubation, the solution in each of the wells was discarded and then, each of the wells was washed five times with a TBS solution containing 0.02% polyoxyethylene (20) sorbitan monolaurate, to thereby prepare a reverse transcriptase-bound plate. Using a control prepared by substantially the same procedure as in item (7) above in Example 7, substantially the same procedure as mentioned above was conducted. Then, substantially the same procedure as in the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 10, were used. Results are shown in Table 10.

TABLE 10

| Type of | Residual activity of reverse transcriptase (%) | | | | | | | | | |
|---|---|---|---|---|---|---|---|---|---|---|
| | HIV-positive person | | | | | HIV-negative person | | | | |
| poly A | H.M. | T.A. | J.O. | S.S. | T.M. | I.K. | R.Y. | K.Y. | T.K. | T.I. |
| Oligo A$_{12-18}$ | 18.5 | 14.5 | 5.5 | 3.3 | 2.4 | 130.5 | 121.0 | 141.6 | 130.7 | 117.7 |
| Poly A | 18.3 | 18.4 | 9.7 | 7.1 | 0.6 | 133.2 | 125.4 | 130.5 | 131.3 | 119.7 |

*Each combination of two letters in the above table individually represents the initials of the person who offered serum for testing.

As shown in Table 10, the antibodies, which were individually, irreversibly bound to the reverse transcriptase to thereby inhibit the binding of the reverse transcriptase to the template-primer (oligo dT·poly A), were individually, quantitatively determined with respect to the residual enzyme activity of the reverse transcriptase. The antibodies could be detected in any poly A length indicated in Table 10.

EXAMPLE 11

By substantially the same procedure as in the "preparation of an oligo dT·poly A-immobilized plate" mentioned in item (6) above in Example 7, an oligo dT·poly A-immobilized plate was prepared. Substantially the same procedure as in the "binding of a reverse transcriptase to the oligo dT·poly A immobilized on the plate" mentioned in item (7) above in Example 7 was repeated, except that the concentration of magnesium chloride was 50 mM, and each of 0.2, 2, 20, 200, 2,000, 20,000 and 200,000 mU/100 µl reverse transcriptases was individually used. After the antigen-antibody reaction, 100 µl of each of the resultant reaction mixtures was individually placed in each well of the oligo dT·poly A-immobilized plate prepared as mentioned above, followed by incubation at 37° C. for 1 hour. After the incubation, the solution in each of the wells was discarded and then, each of the wells was washed five times with a TBS solution containing 0.02% polyoxyethylene (20) sorbitan monolaurate, to thereby prepare a reverse transcriptase-bound plate. Using a control prepared by substantially the same procedure as in item (7) above in Example 7, substantially the same procedure as mentioned above was conducted. Then, substantially the same procedure in the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 11, were used.

On the other hand, substantially the same procedure as mentioned above was repeated, except that 0.2, 2 and 20 μU/100 μl HIV-1 reverse transcriptases were individually used, and that, instead of 2 hours, a reverse transcriptase reaction was performed for 24 hours. Results are shown in Table 11.

TABLE 11

| Amount of reverse transcriptase | Residual activity of reverse transcriptase (%) Samples | | | | |
| --- | --- | --- | --- | --- | --- |
| | M.S. | H.H. | N.T. | Y.I. | Y.Y. |
| ($\mu$U/100 $\mu$l) | | | | | |
| 0.1 | 0.1 | 0.1 | 0.1 | 0.1 | 0.2 |
| 1 | 2.1 | 0.2 | 0.2 | 0.1 | 0.2 |
| 10 | 3.9 | 0.5 | 1.3 | 0.1 | 0.4 |
| (mU/100 $\mu$l) | | | | | |
| 0.1 | 5.4 | 3.5 | 0.2 | 1.2 | 4.3 |
| 1 | 13.1 | 8.8 | 3.1 | 4.4 | 10.2 |
| 10 | 15.5 | 22.6 | 10.2 | 6.0 | 15.7 |
| 100 | 29.2 | 42.6 | 42.2 | 17.1 | 23.3 |
| 1,000 | 51.7 | 69.1 | 60.2 | 28.5 | 33.1 |
| 10,000 | 80.7 | 88.3 | 82.2 | 45.3 | 51.4 |
| 100,000 | 96.4 | 97.6 | 92.3 | 78.6 | 76.2 |

*Each combination of two letters in the above table individually represents the initials of the person who offered serum for testing.

As shown in Table 11, the antibodies, which were individually, irreversibly bound to the reverse transcriptase to thereby inhibit the binding of the reverse transcriptase to the template-primer (oligo dT·poly A), were individually, quantitatively determined with respect to the residual enzyme activity of the reverse transcriptase. The antibodies could be detected in any reverse transcriptase concentration indicated in Table 11.

EXAMPLE 12

By substantially the same procedure as in the "preparation of an oligo dT·poly A-immobilized plate" mentioned in item (6) above in Example 7, an oligo dT·poly A-immobilized plate was prepared. Substantially the same procedure as in the "binding of a reverse transcriptase to the oligo dT·poly A immobilized on the plate" mentioned in item (7) above in Example 7 was repeated, except that the concentration of magnesium chloride was 50 mM, and each of the sampled sera was individually diluted 2-fold, 20-fold, 200-fold, 2,000-fold, 20,000-fold and 200,000-fold. After the antigen-antibody reaction, 100 μl of each of the resultant reaction mixtures was individually placed in each well of the oligo dT·poly A-immobilized plate prepared as mentioned above, followed by incubation at 37° C. for 1 hour. After the incubation, the solution in each of the wells was discarded and then, each of the wells was washed five times with a TBS solution containing 0.02% polyoxyethylene (20) sorbitan monolaurate, to thereby prepare a reverse transcriptase-bound plate. Using a control prepared by substantially the same procedure as in item (7) above in Example 7, substantially the same procedure as mentioned above was conducted. Then, substantially the same procedure as in the "detection of reverse transcriptase activity" mentioned in item (4) above in Example 1 and the "quantitative determination of the antibody having the ability to inhibit the activity of the reverse transcriptase" mentioned in item (5) above in Example 1 was repeated, except that the reverse transcriptase-bound plates and the control, both prepared in this Example 12, were used. Results are shown in Table 12.

TABLE 12

| Serum dilution ratio (fold) | Residual activity of reverse transcriptase (%) | | | | | | | | | |
| --- | --- | --- | --- | --- | --- | --- | --- | --- | --- | --- |
| | HIV-positive person | | | | | HIV-negative person | | | | |
| | M.S. | H.H. | N.T. | Y.I. | Y.Y. | I.K. | R.Y. | K.Y. | T.K. | T.I. |
| 1 | 0.2 | 0.2 | 0.2 | 0.1 | 0.1 | 99.2 | 109.1 | 101.1 | 101.9 | 100.9 |
| 10 | 0.2 | 0.3 | 0.2 | 0.5 | 1.4 | 133.2 | 123.4 | 130.5 | 131.3 | 119.7 |
| 100 | 12.7 | 12.2 | 11.1 | 0.6 | 5.3 | 110.2 | 121.3 | 110.7 | 111.2 | 105.2 |
| 1,000 | 24.7 | 23.4 | 60.2 | 3.3 | 15.8 | 108.3 | 138.2 | 118.0 | 108.2 | 111.2 |
| 10,000 | 46.2 | 55.5 | 74.1 | 25.3 | 31.5 | 109.4 | 113.5 | 119.2 | 120.3 | 110.3 |
| 100,000 | 82.0 | 84.7 | 94.3 | 69.5 | 58.5 | 104.9 | 114.2 | 100.2 | 101.1 | 100.1 |

*Each combination of two letters in the above table individually represents the initials of the person who offered serum for testing.

As shown in Table 12, the antibodies, which were individually, irreversibly bound to the reverse transcriptase to thereby inhibit the binding of the reverse transcriptase to the template-primer (oligo dT·poly A), were individually, quantitatively determined with respect to the residual enzyme activity of the reverse transcriptase. The antibodies could be detected in any serum dilution ratio indicated in Table 12.

EXAMPLE 13

(9) Preparation of an oligo dT·poly A-immobilized plate

By substantially the same procedure as in the "preparation of an oligo dT·poly A-immobilized plate" mentioned in item (1) above in Example 1, an oligo dT·poly A-immobilized plate was prepared.

(10) Binding of a reverse transcriptase to the oligo dT·poly A immobilized on the plate Using the prepared oligo dT·poly A-immobilized plate, a reverse transcriptase-bound plate was prepared by substantially the same procedure as in the "binding of a reverse transcriptase to the oligo dT·poly A immobilized on the plate" mentioned in item (2) above in Example 1.

(11) Antigen-antibody reaction and reverse transcriptase reaction

Sera were respectively sampled from five hemophiliacs infected with HIV and five persons free from HIV infection. Each of the sampled sera was diluted 100-fold with 10 mM phosphate buffer (pH 7.4), containing 150 mM sodium chloride and 0.1% Triton X-100, to thereby obtain test samples. 50 µl of each of the obtained test samples was individually placed in each well of the reverse transcriptase-bound plate as prepared in item (10) above. Immediately thereafter, 50 µl of an aqueous solution, which contained 180 mM HEPES (pH 7.8), 252 mM potassium chloride, 18 mM magnesium chloride, 0.9 mM dithiothreitol, 2.16 mM reduced glutathione, 2% Triton X-100, 3.6% ethylene glycol, 234 µM deoxythymidine triphosphate (dTTP) and 6 µM biotinylated deoxyuridine triphosphate (Bio-dUTP; manufactured and sold by Boehringer-Mannheim GmbH, Germany), was placed in each well of the reverse transcriptase-bound plate, followed by incubation at 37° C. for 2 hours. After the incubation, 10 µl of a 5M sodium chloride solution was placed in each well of the plate and then, the plate was allowed to stand at room temperature for 5 minutes. Then, the solution in each of the wells was discarded, followed by washing of each of the wells five times with a TBS solution containing 0.02% polyoxyethylene (20) sorbitan monolaurate. On the other hand, a control was prepared in substantially the same manner as described above, except that, instead of the test sample prepared above, 100 µl of a solution containing 10 mM phosphate buffer solution (pH 7.4), 150 mM sodium chloride and 0.1% Triton X-100 was used.

100 µl of a 20,000-fold dilution of alkaline phosphatase labeled-streptoavidin (manufactured and sold by Jackson Immuno Research Laboratory Co., U.S.A.), prepared using 50 mM Tris-HCl buffer (pH 7.5) containing 0.5M sodium chloride, 5 mM magnesium chloride and 2% bovine serum albumin, was placed in each well of the plate, followed by incubation at 37° C. for 1 hour. Then, the wells of the plate were washed five times with a TBS solution containing 0.02% polyoxyethylene (20) sorbitan monolaurate.

After washing the wells, 150 µl of diethanolamine-HCl buffer (pH 9.5) containing 1 mM magnesium chloride and 1 mg/ml para-nitrophenyl phosphate disodium (manufactured and sold by Sigma Chemical Company, U.S.A) was placed in each of the wells, followed by incubation at 37° C. for 30 minutes. Subsequently, 50 µl of a 1N aqueous sodium hydroxide solution was added to each of the wells to thereby detect the biotinylated DNA which is a product of the reverse transcriptase reaction. With respect to each of the biotinylated DNA, an absorbance value at 405 nm was measured by means of a plate reader. Then, substantially the same procedure as in the "quantitative determination of the antibody having the ability to inhibit the activity of the reverse transcriptase" mentioned in item (5) above in Example 1 was repeated, except that the reverse transcriptase-bound plates and the control, both prepared in Example 13, were used. Results are shown in Table 13.

TABLE 13

| Magnesium concentration | Residual activity of reverse transcriptase (%) | | | | | | | | | |
|---|---|---|---|---|---|---|---|---|---|---|
| | HIV-positive person | | | | | HIV-negative person | | | | |
| (mM) | F.O. | Y.U. | S.T. | K.A. | Y.K. | I.K. | R.Y. | K.Y. | T.K. | T.I. |
| 0.01 | 18.4 | 36.5 | 58.4 | 59.1 | 86.6 | 113.4 | 104.8 | 105.3 | 109.0 | 103.3 |
| 0.1 | 14.1 | 29.2 | 54.3 | 59.0 | 83.9 | 103.3 | 99.4 | 122.2 | 109.3 | 109.4 |
| 1 | 15.0 | 27.4 | 55.7 | 52.4 | 85.7 | 104.3 | 105.5 | 101.7 | 102.2 | 109.8 |
| 10 | 19.9 | 29.3 | 59.8 | 58.8 | 89.9 | 92.7 | 112.9 | 103.4 | 108.2 | 105.2 |
| 100 | 13.2 | 33.4 | 53.4 | 59.2 | 82.3 | 108.2 | 104.3 | 102.3 | 109.1 | 110.0 |
| 1,000 | 18.2 | 32.2 | 58.1 | 56.3 | 86.2 | 102.3 | 116.8 | 105.6 | 126.2 | 125.1 |

*Each combination of two letters in the above table individually represents the initials of the person who offered serum for testing.

As shown in Table 13, the antibodies, which were individually bound to the reverse transcriptase which is synthesizing a DNA to thereby inhibit the chain elongation of a complementary DNA to the template RNA, were individually, quantitatively determined with respect to the residual enzyme activity of the reverse transcriptase. The antibodies could be detected in any magnesium ion concentration indicated in Table 13.

Further, the quantitative determination of the antibodies was separately conducted using the plate prepared using a solution containing 0 mM magnesium chloride, 0.1% Triton X-100 and 5 mU/100 µl reverse transcriptase in the "binding reaction of the reverse transcriptase to the oligo dT·poly A immobilized on the plate" mentioned in item (10) above. With respect to the test samples prepared using the sera of the HIV-infected persons, the residual activities of the reverse transcriptase were 33.2% for H. K., 28.4% for K. K. and 49.2% for K. S., whereas with respect to the test samples prepared using the sera of the HIV-uninfected persons, the residual activities of the reverse transcriptase were 102.6% for M. T., 106.5% for T. E. and 107.1% for T. T.

EXAMPLE 14

By substantially the same procedure as in the "preparation of an oligo dT·poly A-immobilized plate" mentioned in item (9) above in Example 13, an oligo dT·poly A-immobilized plate was prepared. Using the prepared oligo dT·poly A-immobilized plate, substantially the same procedure as in the "binding of a reverse transcriptase to the oligo dT·poly A immobilized on the plate" mentioned in item (10) above in Example 13 was repeated, except that, instead of magnesium chloride, each of manganese chloride and calcium chloride was individually used, to thereby prepare reverse transcriptase-bound plates. Substantially the same procedure as in the "antigen-antibody reaction and reverse transcriptase reaction" mentioned in item (11) above in Example 13 was repeated, except that the reverse transcriptase-bound plates prepared as mentioned above were used. Then, substantially the same procedure as in the "quantitative determination of the antibody having the ability to inhibit the activity of the reverse transcriptase" mentioned in item (5) above in Example 1 was repeated, except that the reverse transcriptase-bound plates and the control, both prepared in this Example 14, were used. Results are shown in Table 14.

ions and in any metal ion concentrations indicated in Table 14.

EXAMPLE 15

Oligo dT·poly A-immobilized plates were prepared by substantially the same procedure as in the "preparation of an oligo dT·poly A-immobilized plate" mentioned in item (9) above in Example 13, except that, instead of the oligo $dT_{19-24}$, each of oligo $dT_5$, oligo $dT_{10}$ (manufactured and sold by Sigma Chemical Company, U.S.A), oligo $dT_{25-30}$ and poly dT (average chain length: 794 nucleotides) (manufactured and sold by Pharmacia Fine Chemicals AB, Sweden) was individually used. Using the prepared oligo dT·poly A-immobilized plates, substantially the same procedure as in the "binding of a reverse transcriptase to the oligo dT·poly A immobilized on the plate" mentioned in item (10) above in Example 13 was repeated, except that the concentration of magnesium chloride was 50 mM, to thereby prepare reverse transcriptase-bound plates. Substantially the same procedure as in the "antigen-antibody reaction and reverse transcriptase reaction" mentioned in item (11) above in Example 13 was repeated, except that the reverse transcriptase-bound plates prepared as mentioned

TABLE 14

| | Residual activity of reverse transcriptase (%) | | | | | | | | | |
|---|---|---|---|---|---|---|---|---|---|---|
| | HIV-positive person | | | | | HIV-negative person | | | | |
| | F.O. | Y.U. | S.T. | K.A. | Y.K. | I.K. | R.Y. | K.Y. | T.K. | T.I. |
| Manganese concentration (mM) | | | | | | | | | | |
| 0.01 | 21.3 | 25.3 | 54.3 | 59.9 | 74.4 | 106.2 | 102.6 | 105.5 | 112.4 | 112.8 |
| 0.1 | 21.0 | 28.8 | 51.9 | 62.4 | 78.0 | 108.4 | 103.5 | 109.5 | 112.0 | 102.9 |
| 1 | 22.4 | 29.3 | 52.5 | 61.0 | 72.3 | 109.4 | 102.9 | 101.9 | 123.3 | 101.4 |
| 10 | 21.9 | 26.4 | 56.2 | 63.8 | 71.9 | 102.6 | 114.5 | 106.9 | 114.5 | 109.5 |
| 100 | 20.4 | 36.3 | 55.3 | 59.1 | 84.6 | 119.4 | 105.8 | 105.3 | 103.0 | 103.8 |
| 1,000 | 20.9 | 28.2 | 61.0 | 58.2 | 78.1 | 119.9 | 104.0 | 102.0 | 108.1 | 105.3 |
| Calcium concentration (mM) | | | | | | | | | | |
| 0.01 | 32.0 | 15.1 | 57.4 | 62.9 | 89.1 | 116.2 | 105.7 | 118.3 | 119.5 | 104.6 |
| 0.1 | 39.1 | 21.5 | 54.6 | 71.8 | 93.4 | 126.9 | 100.4 | 115.2 | 126.3 | 107.4 |
| 1 | 31.5 | 24.3 | 52.4 | 69.6 | 92.9 | 121.1 | 105.2 | 115.3 | 114.2 | 104.3 |
| 10 | 35.4 | 26.9 | 55.7 | 68.2 | 85.8 | 129.5 | 113.5 | 112.4 | 105.4 | 101.6 |
| 100 | 30.7 | 22.8 | 59.1 | 68.9 | 96.0 | 127.0 | 115.9 | 117.7 | 113.2 | 111.8 |
| 1,000 | 31.0 | 28.8 | 64.1 | 67.2 | 88.6 | 119.7 | 124.3 | 107.0 | 128.1 | 112.9 |

*Each combination of two letters in the above table individually represents the initials of the person who offered serum for testing.

As shown in Table 14, the antibodies, which were individually bound to the reverse transcriptase which is synthesizing a DNA to thereby inhibit the chain elongation of a complementary DNA to the template RNA, were individually, quantitatively determined with respect to the residual enzyme activity of the reverse transcriptase. Thantibodies could be detected in the presence of any metal e above were used. Then, substantially the same procedure as in the "quantitative determination of the antibody having the ability to inhibit the activity of the reverse transcriptase" mentioned in item (5) above in Example 1 was repeated, except that the reverse transcriptase-bound plates and the control, both prepared in this Example 15, were used. Results are shown in Table 15.

TABLE 15

| Type of oligo dT | Residual activity of reverse transcriptase (%) | | | | | | | | | |
|---|---|---|---|---|---|---|---|---|---|---|
| | HIV-positive person | | | | | HIV-negative person | | | | |
| | H.M. | T.A. | J.O. | S.S. | T.M. | I.K. | R.Y. | K.Y. | T.K. | T.I. |
| Oligo dT$_5$ | 15.2 | 62.5 | 61.9 | 81.4 | 11.2 | 110.2 | 125.3 | 129.2 | 125.1 | 111.5 |
| Oligo dT$_{10}$ | 14.5 | 65.4 | 57.5 | 82.9 | 27.5 | 104.3 | 113.2 | 119.9 | 113.0 | 100.3 |
| Oligo dT$_{25-30}$ | 14.3 | 63.4 | 60.0 | 75.9 | 20.9 | 108.3 | 131.2 | 114.3 | 112.8 | 108.2 |
| Poly dT | 11.1 | 71.1 | 58.5 | 88.3 | 28.0 | 109.3 | 111.5 | 113.4 | 121.0 | 120.1 |

*Each combination of two letters in the above table individually represents the initials of the person who offered serum for testing.

As shown in Table 15, the antibodies, which were individually bound to the reverse transcriptase which is synthesizing a DNA to thereby inhibit the chain elongation of a complementary DNA to the template RNA, were individually, quantitatively determined with respect to the residual enzyme activity of the reverse transcriptase. The antibodies could be detected in any oligo dT length indicated in Table 15.

EXAMPLE 16

Oligo dT·poly A-immobilized plates were prepared by substantially the same procedure as in the "preparation of an oligo dT·poly A-immobilized plate" mentioned in item (9) above in Example 13, except that, instead of the poly A, each of oligo A$_{12-18}$ and poly A (average chain length: 534 nucleotides) (manufactured and sold by Pharmacia Fine Chemicals AB, Sweden) was individually used. Using the prepared oligo dT·poly A-immobilized plates, substantially the same procedure as in the "binding of a reverse transcriptase to the oligo dT·poly A immobilized on the plate" mentioned in item (10) above in Example 13 was repeated, except that the concentration of magnesium chloride was 50 mM, to thereby prepare reverse transcriptase-bound plates. Substantially the same procedure as in the "antigen-antibody reaction and reverse transcriptase reaction" mentioned in item (11) above in Example 13 was repeated, except that the reverse transcriptase-bound plates prepared as mentioned above were used. Then, substantially the same procedure as in the "quantitative determination of the antibody having the ability to inhibit the activity of the reverse transcriptase" mentioned in item (5) above in Example 1 was repeated, except that the reverse transcriptase-bound plates and the control, both prepared in this Example 16, were used. Results are shown in Table 16.

As shown in Table 16, the antibodies, which were individually bound to the reverse transcriptase which is synthesizing a DNA to thereby inhibit the chain elongation of a complementary DNA to the template RNA, were individually, quantitatively determined with respect to the residual enzyme activity of the reverse transcriptase. The antibodies could be detected in any poly A length indicated in Table 16.

EXAMPLE 17

By substantially the same procedure as in the mentioned "preparation of an oligo dT·poly A-immobilized plate" mentioned in item (9) above in Example 13, an oligo dT·poly A-immobilized plate was prepared. Using the prepared oligo dT·poly A-immobilized plate, substantially the same procedure as in the "binding of a reverse transcriptase to the oligo dT·poly A immobilized on the plate" mentioned in item (10) above in Example 13 was repeated, except that the concentration of magnesium chloride was 50 mM, and each of 0.1, 1, 10, 100, 1,000, 10,000 and 100,000 mU/100 µl reverse transcriptases was individually used, to thereby prepare reverse transcriptase-bound plates. Substantially the same procedure as in the "antigen-antibody reaction and reverse transcriptase reaction" mentioned in item (11) above in Example 13 was repeated, except that the reverse transcriptase-bound plates prepared as mentioned above were used. Then, substantially the same procedure as in the "quantitative determination of the antibody having the ability to inhibit the activity of the reverse transcriptase" mentioned in item (5) above in Example 1 was repeated, except that the reverse transcriptase-bound plates and the control, both prepared in this Example 5, were used.

On the other hand, substantially the same procedure as mentioned above was repeated, except that 0.1, 1 and 10 µU/100 µl HIV-1 reverse transcriptases were individually used, and that, instead of 2 hours, a reverse transcriptase reaction was performed for 24 hours. Results are shown in Table 17.

TABLE 16

| Type of poly A | Residual activity of reverse transcriptase (%) | | | | | | | | | |
|---|---|---|---|---|---|---|---|---|---|---|
| | HIV-positive person | | | | | HIV-negative person | | | | |
| | H.M. | T.A. | J.O. | S.S. | T.M. | I.K. | R.Y. | K.Y. | T.K. | T.I. |
| Oligo A$_{12-18}$ | 28.1 | 48.1 | 29.3 | 71.0 | 41.6 | 113.7 | 115.4 | 114.9 | 135.5 | 129.9 |
| Poly A | 26.5 | 54.5 | 35.7 | 73.2 | 43.1 | 120.4 | 114.2 | 111.6 | 120.6 | 124.3 |

*Each combination of two letters in the above table individually represents the initials of the person who offered serum for testing.

TABLE 17

| Amount of reverse transcriptase | Residual activity of reverse transcriptase (%) Samples | | | | |
|---|---|---|---|---|---|
| | M.S. | H.H. | N.T. | Y.I. | Y.Y. |
| ($\mu$U/100$\mu$l) | | | | | |
| 0.1 | 0.5 | 0.2 | 0.2 | 0.1 | 0.2 |
| 1 | 0.2 | 0.4 | 0.2 | 0.1 | 2.3 |
| 10 | 0.3 | 0.9 | 0.3 | 0.1 | 2.6 |
| (mU/100$\mu$l) | | | | | |
| 0.1 | 5.2 | 3.4 | 4.2 | 2.2 | 5.9 |

TABLE 17-continued

| Amount of reverse transcriptase | Residual activity of reverse transcriptase (%) Samples | | | | |
|---|---|---|---|---|---|
| | M.S. | H.H. | N.T. | Y.I. | Y.Y. |
| 1 | 11.1 | 7.1 | 10.1 | 6.8 | 13.2 |
| 10 | 35.2 | 11.5 | 15.2 | 10.0 | 25.4 |
| 100 | 49.2 | 31.2 | 33.2 | 18.1 | 39.3 |
| 1,000 | 71.2 | 58.7 | 53.2 | 48.4 | 71.9 |
| 10,000 | 80.2 | 76.7 | 69.2 | 65.3 | 80.2 |
| 100,000 | 88.3 | 85.4 | 86.3 | 88.8 | 86.8 |

* Each combination of two letters in the above table individually represents the initials of the person who offered serum for testing.

As shown in Table 17, the antibodies, which were individually bound to the reverse transcriptase which is synthesizing a DNA to thereby inhibit the chain elongation of a complementary DNA to the template RNA, were individually, quantitatively determined with respect to the residual enzyme activity of the reverse transcriptase. The antibodies could be detected in any reverse transcriptase concentration indicated in Table 17.

EXAMPLE 18

By substantially the same procedure as in the "preparation of an oligo dT·poly A-immobilized plate" mentioned in item (9) above in Example 13, an oligo dT·poly A-immobilized plate was prepared. Using the prepared oligo dT·poly A-immobilized plate, substantially the same procedure as in the "binding of a reverse transcriptase to the oligo dT·poly A immobilized on the plate" mentioned in item (10) above in Example 13 was repeated, except that the concentration of magnesium chloride was 50 mM, to thereby prepare reverse transcriptase-bound plates. Using the prepared reverse transcriptase-bound plate, substantially the same procedure as in the "reaction of a test sample with the reverse transcriptase-bound plate" mentioned in item (11) above in Example 13 was repeated, except that each of the sampled sera was individually diluted 1-fold, 10-fold, 100-fold, 1,000-fold, 10,000-fold and 100,000-fold. Then, substantially the same procedure as in the "quantitative determination of the antibody having the ability to inhibit the activity of the reverse transcriptase" mentioned in item (5) above in Example 1 was repeated, except that the reverse transcriptase-bound plates and the control, both prepared in this Example 18, were used. Results are shown in Table 18.

TABLE 18

| Serum dilution ratio (fold) | Residual activity of reverse transcriptase (%) | | | | | | | | | |
|---|---|---|---|---|---|---|---|---|---|---|
| | HIV-positive person | | | | | HIV-negative person | | | | |
| | M.S. | H.H. | N.T. | Y.I. | Y.Y. | I.K. | R.Y. | K.Y. | T.K. | T.I. |
| 1 | 0.1 | 0.1 | 0.2 | 1.1 | 0.4 | 104.2 | 106.2 | 100.3 | 101.0 | 101.9 |
| 10 | 2.2 | 1.5 | 2.2 | 9.2 | 5.4 | 102.4 | 111.2 | 115.2 | 120.5 | 112.3 |
| 100 | 9.7 | 22.3 | 31.5 | 16.7 | 35.3 | 113.2 | 125.5 | 110.7 | 111.2 | 107.2 |
| 1,000 | 24.2 | 43.8 | 50.2 | 23.2 | 65.9 | 104.2 | 101.2 | 100.1 | 100.1 | 102.1 |
| 10,000 | 53.2 | 75.9 | 64.2 | 43.2 | 81.2 | 109.3 | 131.2 | 113.0 | 108.3 | 112.2 |
| 100,000 | 78.0 | 85.5 | 74.3 | 58.0 | 97.8 | 100.9 | 113.3 | 119.1 | 100.5 | 100.3 |

* Each combination of two letters in the above table individually represents the initials of the person who offered serum for testing.

As shown in Table 18, the antibodies, which were individually bound to the reverse transcriptase which is synthesizing a DNA to thereby inhibit the chain elongation of a complementary DNA to the template RNA, were individually, quantitatively determined with respect to the residual enzyme activity of the reverse transcriptase. The antibodies could be detected in any serum dilution ratio indicated in Table 18.

INDUSTRIAL APPLICABILITY

The present invention provides an easy and highly reproducible method for classifying into three groups and quantitatively determining the antibodies against the epitopes of a viral reverse transcriptase. Using the method of the present invention, not only the virus which has mutated during a latent period thereof, and the properties which the virus exhibits as a result of the mutation, but also a virus which has acquired drug resistance as a result of the administration of the drugs to host, can be studied by quantitatively determining the antibodies. Further, it has also become possible to accurately and promptly determine the changes in the infected host, such as the change in the ability to produce antibodies, which occur in accordance with the progression of illness. In addition, the method of the present invention is advantageous in that the biological samples used are easily available, and that cumbersome procedures, such as culturing of the virus, are not required. Therefore, the method of the present invention is effective for the diagnosis and the like of HIV which necessarily include testing for an extremely large number of test items. Further, the method of the present invention can be advantageously used for the study of HIV infection because an antibody is more stable than a viral antigen and a high biosafety can be achieved by the treatment of the biological samples with a surfactant.

I claim:

1. A method for quantitatively determining an antibody, contained in a biological sample, having the ability to inhibit the activity of a reverse transcriptase obtained from a human immunodeficiency virus (HIV), which comprises the steps of:
   (A) reacting a hybridization product of a primer consisting essentially of oligodeoxythymine nucleotide immobilized on a solid phase and an RNA template consisting essentially of adenine ribopolynucleotide with a reverse transcriptase obtained from HIV in an aqueous reaction system, to bind said reverse transcriptase to said hybridization product, thereby obtaining a first reaction mixture containing a hybridization product-bound reverse transcriptase,
   said reaction at step (A) being conducted in the presence of a water-soluble metal salt capable of producing bivalent metal ions selected from the group consisting of magnesium ions, calcium ions, manganese ions and mixtures thereof,
   wherein said bivalent metal ions are present in a concentration of from 0.1 mM to 500 mM in said aqueous reaction system,
   (B) removing the reverse transcriptase remaining unreacted from said first reaction mixture by washing, and reacting a biological sample containing an antibody having the ability to inhibit the activity of a reverse transcriptase obtained from HIV with said hybridization product-bound reverse transcriptase, to bind said antibody to said hybridization product-bound reverse transcriptase, thereby obtaining a second reaction mixture containing the antibody which is bound to said hybridization product-bound reverse transcriptase,
   (C) removing the antibody remaining unreacted from said second reaction mixture by washing, and adding a deoxymononucleotide triphosphate to the remainder of said second reaction mixture to thereby synthesize a deoxyribonucleic acid complementary to said RNA template, and
   (D) measuring the amount of the synthesized complementary deoxyribonucleic acid and quantitatively determining the antibody having the ability to inhibit the activity of the reverse transcriptase, based on the measured amount of said synthesized complementary deoxyribonucleic acid.

2. The method according to claim 1, wherein said primer consisting essentially of oligodeoxythymine nucleotide comprises from 5 to 100,000 nucleotides.

3. The method according to claim 1, wherein said RNA template consisting essentially of adenine ribopolynucleotide comprises from 5 to 100,000 nucleotides.

4. The method according to claim 1, wherein, at step (A), said reverse transcriptase is used in an amount of from 2 $\mu$U/ml to 1,000 U/ml of said aqueous reaction system.

5. The method according to claim 1, wherein said deoxymononucleotide triphosphate is biotinylated deoxyuridine triphosphate.

6. The method according to claim 1, wherein said biological sample is obtained by diluting human serum or plasma in a dilution ratio in the range of from 1-fold to 100,000-fold.

7. A method for quantitatively determining an antibody, contained in a biological sample, having the ability to inhibit the activity of a reverse transcriptase obtained from a human immunodeficiency virus (HIV), which comprises the steps of:
   (A) reacting a biological sample containing an antibody having the ability to inhibit the activity of a reverse transcriptase obtained from HIV with a reverse transcriptase obtained from HIV in an aqueous reaction system, to bind said reverse transcriptase to said antibody, thereby obtaining a first reaction mixture containing an antibody-bound reverse transcriptase,
   (B) reacting a hybridization product of a primer consisting essentially of oligodeoxythymine nucleotide immobilized on a solid phase and an RNA template consisting essentially of adenine ribopolynucleotide with said first reaction mixture, to bind the reverse transcriptase to said hybridization product, thereby obtaining a second reaction mixture containing a hybridization product-bound reverse transcriptase,
   said reaction at step (B) being conducted in the presence of a water-soluble metal salt capable of producing bivalent metal ions selected from the group consisting of magnesium ions, calcium ions, manganese ions and mixtures thereof,
   wherein said bivalent metal ions are present in a concentration of from 0.1 mM to 500 mM in said aqueous reaction system,
   (C) removing all reactants remaining unreacted from said second reaction mixture by washing, and adding a deoxymononucleotide triphosphate to the remainder of said second reaction mixture to thereby synthesize a deoxyribonucleic acid complementary to said RNA template, and
   (D) measuring the amount of the synthesized complementary deoxyribonucleic acid and quantitatively determining the antibody having the ability to inhibit the activity of the reverse transcriptase, based on the measured amount of said synthesized complementary deoxyribonucleic acid.

8. The method according to claim 7, wherein said primer consisting essentially of oligodeoxythymine nucleotide comprises from 5 to 100,000 nucleotides.

9. The method according to claim 7, wherein said template RNA consisting essentially of adenine ribopolynucleotide comprises from 5 to 100,000 nucleotides.

10. The method according to claim 7, wherein, at step (A), said reverse transcriptase is used in an amount of from 2 $\mu$U/ml to 1,000 U/mi of said aqueous reaction system.

11. The method according to claim 7, wherein said deoxymononucleotide triphosphate is biotinylated deoxyuridine triphosphate.

12. The method according to claim 7, wherein said biological sample is obtained by diluting human serum or plasma in a dilution ratio in the range of from 1-fold to 100,000-fold.

* * * * *